(12) United States Patent
Tamarkin et al.

(10) Patent No.: US 7,820,145 B2
(45) Date of Patent: Oct. 26, 2010

(54) OLEAGINOUS PHARMACEUTICAL AND COSMETIC FOAM

(75) Inventors: Dov Tamarkin, Maccabim (IL); Doron Friedman, Karmei Yosef (IL); Meir Eini, Ness Ziona (IL); Alex Besonov, Rehovet (IL)

(73) Assignee: Foamix Ltd., Ness Ziona (IL)

( * ) Notice: Subject to any disclaimer, the term of this patent is extended or adjusted under 35 U.S.C. 154(b) by 1562 days.

(21) Appl. No.: 10/835,505

(22) Filed: Apr. 28, 2004

(65) Prior Publication Data

US 2005/0031547 A1 Feb. 10, 2005

Related U.S. Application Data

(60) Provisional application No. 60/530,015, filed on Dec. 16, 2003, provisional application No. 60/492,385, filed on Aug. 4, 2003.

(51) Int. Cl.
*A61K 9/12* (2006.01)
(52) U.S. Cl. .......................................... 424/45
(58) Field of Classification Search ........................ None
See application file for complete search history.

(56) References Cited

U.S. PATENT DOCUMENTS

| | | |
|---|---|---|
| 1,924,972 A | 8/1933 | Beckert |
| 2,085,733 A | 7/1937 | Bird |
| 2,390,921 A | 12/1945 | Clark |
| 2,586,287 A | 2/1952 | Apperson |
| 2,617,754 A | 11/1952 | Neely |
| 2,968,628 A | 1/1961 | Reed |
| 3,062,715 A | 11/1962 | Reese |
| 3,092,255 A | 6/1963 | Hohman |
| 3,092,555 A | 6/1963 | Fisher et al. |
| 3,141,821 A | 7/1964 | Compeau |
| 3,142,420 A | 7/1964 | Gawthrop |
| 3,178,352 A | 4/1965 | Erickson |
| 3,236,457 A | 4/1966 | Sunnen et al. |
| 3,244,589 A | 4/1966 | Sunnen |
| 3,252,859 A | 5/1966 | Silver |
| 3,261,695 A | 7/1966 | Sienciewicz |
| 3,263,869 A | 8/1966 | Corsette |
| 3,301,444 A | 1/1967 | Wittke |
| 3,303,970 A | 2/1967 | Breslau et al. |
| 3,369,034 A | 2/1968 | Chalmers |
| 3,384,541 A | 5/1968 | Clark et al. |
| 3,395,215 A | 7/1968 | Warren |
| 3,401,849 A | 9/1968 | Weber, III |
| 3,419,658 A | 12/1968 | Amsdon |
| 3,559,890 A | 2/1971 | Brooks et al. |
| 3,561,262 A | 2/1971 | Borocki |
| 3,574,821 A | 4/1971 | Pfirrmann |
| 3,577,518 A | 5/1971 | Shepherd |
| 3,751,562 A | 8/1973 | Nichols |
| 3,770,648 A | 11/1973 | Mackes |
| 3,787,566 A | 1/1974 | Gauvreau |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,959,160 A | 5/1976 | Horsler et al. |
| 3,962,150 A | 6/1976 | Viola |
| 3,966,090 A | 6/1976 | Prussin et al. |
| 3,970,584 A | 7/1976 | Hart et al. |
| 3,993,224 A | 11/1976 | Harrison |
| 3,997,467 A | 12/1976 | Jederstrom et al. |
| 4,001,442 A | 1/1977 | Stahlberger et al. |
| 4,019,657 A | 4/1977 | Spitzer et al. |
| 4,110,426 A | 8/1978 | Barnhurst |
| 4,124,149 A | 11/1978 | Spitzer et al. |
| 4,145,411 A | 3/1979 | Mende |
| 4,160,827 A | 7/1979 | Cho et al. |
| 4,213,979 A | 7/1980 | Levine |
| 4,214,000 A | 7/1980 | Papa |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |

(Continued)

FOREIGN PATENT DOCUMENTS

DE 933486 9/1955

(Continued)

OTHER PUBLICATIONS

Barry, B.W. et al, Comparative bio-availability and activity of proprietary topical corticosteroid preparations: vasoconstrictor assays on thirty-one ointments, British Journal of Dermatology, 93, 563-571, 1975.

(Continued)

*Primary Examiner*—Robert A Wax
*Assistant Examiner*—Melissa S Mercier
(74) *Attorney, Agent, or Firm*—Wilmer Cutler Pickering Hale and Dorr LLP

(57) ABSTRACT

The invention relates to stable oleaginous cosmetic or therapeutic foam compositions containing certain active agents, having unique therapeutic properties and methods of treatment using such compositions. The foamable composition includes at least one solvent selected from a hydrophobic solvent, a silicone oil, an emollient, a co-solvent, and mixtures thereof, wherein the solvent is present at a concentration of about 70% to about 96.5% by weight of the total composition, at least a non-ionic surface-active agent at a concentration of about 0.1% to less than about 10% by weight of the total composition; at least one gelling agent at a concentration of about 0.1% to about 5% by weight of the total composition; a therapeutically effective amount of at least one active agent; and at least one liquefied or compressed gas propellant, at a concentration of about 3% to about 25% by weight of the total composition.

67 Claims, No Drawings

U.S. PATENT DOCUMENTS

| | | | |
|---|---|---|---|
| 4,268,499 A | 5/1981 | Keil | |
| 4,271,149 A | 6/1981 | Winicov et al. | |
| 4,299,826 A | 11/1981 | Luedders | |
| 4,323,694 A | 4/1982 | Scala, Jr. | |
| 4,385,161 A | 5/1983 | Caunt et al. | |
| 4,386,104 A | 5/1983 | Nazzaro-Porro | |
| 4,447,486 A | 5/1984 | Hoppe et al. | |
| 4,508,705 A | 4/1985 | Chaudhuri et al. | |
| 4,522,948 A | 6/1985 | Walker | |
| 4,529,601 A | 7/1985 | Broberg et al. | |
| 4,529,605 A | 7/1985 | Lynch et al. | |
| 4,574,052 A | 3/1986 | Gupte et al. | |
| 4,576,961 A | 3/1986 | Lorck et al. | |
| 4,627,973 A | 12/1986 | Moran et al. | |
| 4,628,063 A | 12/1986 | Haines et al. | |
| 4,672,078 A | 6/1987 | Sakai et al. | |
| 4,741,855 A | 5/1988 | Grote et al. | |
| 4,752,465 A | 6/1988 | Mackles | |
| 4,784,842 A | 11/1988 | London et al. | |
| 4,804,674 A | 2/1989 | Curtis-Prior | |
| 4,808,388 A * | 2/1989 | Beutler et al. | 424/47 |
| 4,822,613 A | 4/1989 | Rodero | |
| 4,827,378 A | 5/1989 | Gillan et al. | |
| 4,836,217 A | 6/1989 | Fischer et al. | |
| 4,837,378 A | 6/1989 | Borgman | |
| 4,847,068 A | 7/1989 | Dole et al. | |
| 4,863,900 A | 9/1989 | Pollock et al. | |
| 4,874,794 A | 10/1989 | Katz | |
| 4,885,282 A | 12/1989 | Thornfeldt | |
| 4,913,893 A | 4/1990 | Varco et al. | |
| 4,956,049 A | 9/1990 | Bernheim et al. | |
| 4,957,732 A | 9/1990 | Grollier et al. | |
| 4,963,351 A | 10/1990 | Weston | |
| 4,970,067 A | 11/1990 | Panandiker et al. | |
| 4,981,677 A | 1/1991 | Thau | |
| 4,981,679 A | 1/1991 | Briggs et al. | |
| 4,981,845 A | 1/1991 | Pereira et al. | |
| 4,992,478 A | 2/1991 | Geria | |
| 5,002,680 A | 3/1991 | Schmidt et al. | |
| 5,007,556 A | 4/1991 | Lover | |
| 5,015,471 A | 5/1991 | Birtwistle et al. | |
| 5,034,220 A | 7/1991 | Helioff et al. | |
| 5,053,228 A | 10/1991 | Mori et al. | |
| 5,071,648 A | 12/1991 | Rosenblatt | |
| 5,071,881 A | 12/1991 | Parfondry et al. | |
| 5,087,618 A | 2/1992 | Bodor | |
| 5,089,252 A | 2/1992 | Grollier et al. | |
| 5,094,853 A | 3/1992 | Hagarty | |
| 5,100,917 A | 3/1992 | Flynn et al. | |
| 5,130,121 A | 7/1992 | Kopolow et al. | |
| 5,133,972 A | 7/1992 | Ferrini et al. | |
| 5,135,915 A | 8/1992 | Czarniecki et al. | |
| 5,143,717 A | 9/1992 | Davis | |
| 5,156,765 A | 10/1992 | Smrt | |
| 5,164,357 A | 11/1992 | Bartman et al. | |
| 5,164,367 A | 11/1992 | Pickart | |
| 5,167,950 A | 12/1992 | Lins | |
| 5,171,577 A | 12/1992 | Griat et al. | |
| 5,196,405 A | 3/1993 | Packman | |
| 5,204,093 A | 4/1993 | Victor | |
| 5,208,031 A | 5/1993 | Kelly | |
| 5,217,707 A | 6/1993 | Szabo et al. | |
| 5,219,877 A | 6/1993 | Shah et al. | |
| 5,230,897 A | 7/1993 | Griffin et al. | |
| 5,254,334 A | 10/1993 | Ramirez et al. | |
| 5,262,407 A | 11/1993 | Leveque et al. | |
| 5,279,819 A | 1/1994 | Hayes | |
| 5,300,286 A | 4/1994 | Gee | |
| 5,301,841 A | 4/1994 | Fuchs | |
| 5,308,643 A | 5/1994 | Osipow et al. | |
| 5,314,904 A | 5/1994 | Egidio et al. | |
| 5,326,557 A | 7/1994 | Glover et al. | |
| 5,352,437 A | 10/1994 | Nakagawa et al. | |
| 5,384,308 A | 1/1995 | Henkin | |
| 5,385,943 A | 1/1995 | Nazzaro-Porro | |
| 5,411,992 A | 5/1995 | Eini et al. | |
| 5,422,361 A | 6/1995 | Munayyer et al. | |
| 5,429,815 A | 7/1995 | Faryniarz et al. | |
| 5,435,996 A | 7/1995 | Glover et al. | |
| 5,451,404 A | 9/1995 | Furman | |
| 5,491,245 A | 2/1996 | Gruning et al. | |
| 5,508,033 A | 4/1996 | Briand et al. | |
| 5,512,555 A | 4/1996 | Waldstreicher | |
| 5,520,918 A | 5/1996 | Smith | |
| 5,527,534 A | 6/1996 | Myhling | |
| 5,527,822 A | 6/1996 | Scheiner | |
| 5,529,770 A | 6/1996 | McKinzie et al. | |
| 5,531,703 A | 7/1996 | Skwarek et al. | |
| 5,534,261 A | 7/1996 | Rodgers et al. | |
| 5,536,743 A | 7/1996 | Borgman | |
| 5,540,853 A | 7/1996 | Trinh et al. | |
| 5,545,401 A | 8/1996 | Shanbrom | |
| 5,567,420 A | 10/1996 | McEleney et al. | |
| 5,578,315 A | 11/1996 | Chien et al. | |
| 5,589,515 A | 12/1996 | Suzuki et al. | |
| 5,603,940 A | 2/1997 | Candau et al. | |
| 5,605,679 A | 2/1997 | Hansenne et al. | |
| 5,614,171 A | 3/1997 | Clavenna et al. | |
| 5,635,469 A | 6/1997 | Fowler et al. | |
| 5,641,480 A | 6/1997 | Vermeer | |
| 5,650,554 A | 7/1997 | Moloney | |
| 5,658,749 A | 8/1997 | Thornton | |
| 5,658,956 A | 8/1997 | Martin et al. | |
| 5,663,208 A | 9/1997 | Martin | |
| 5,672,634 A | 9/1997 | Tseng et al. | |
| 5,679,324 A * | 10/1997 | Lisboa et al. | 424/45 |
| 5,683,710 A | 11/1997 | Akemi | |
| 5,700,396 A | 12/1997 | Suzuki et al. | |
| 5,716,611 A | 2/1998 | Oshlack et al. | |
| 5,719,197 A | 2/1998 | Kanios et al. | |
| 5,730,964 A | 3/1998 | Waldstreicher | |
| 5,733,558 A | 3/1998 | Breton et al. | |
| 5,753,245 A | 5/1998 | Fowler | |
| 5,759,520 A | 6/1998 | Sachetto | |
| 5,759,579 A | 6/1998 | Singh et al. | |
| 5,767,104 A | 6/1998 | Bar-Shalom et al. | |
| 5,783,202 A | 7/1998 | Tomlinson et al. | |
| 5,792,922 A | 8/1998 | Moloney | |
| 5,804,546 A | 9/1998 | Hall et al. | |
| 5,817,322 A | 10/1998 | Xu et al. | |
| 5,824,650 A | 10/1998 | De Lacharriere et al. | |
| 5,833,960 A | 11/1998 | Gers-Barlag et al. | |
| 5,837,270 A | 11/1998 | Burgess | |
| 5,840,744 A | 11/1998 | Borgman | |
| 5,843,411 A | 12/1998 | Hernandez et al. | |
| 5,846,983 A | 12/1998 | Sandborn et al. | |
| 5,856,452 A | 1/1999 | Moloney | |
| 5,871,720 A | 2/1999 | Gutierrez et al. | |
| 5,877,216 A | 3/1999 | Place et al. | |
| 5,879,469 A | 3/1999 | Avram et al. | |
| 5,885,581 A | 3/1999 | Massand | |
| 5,889,028 A | 3/1999 | Sandborn et al. | |
| 5,902,574 A | 5/1999 | Stoner et al. | |
| 5,902,789 A | 5/1999 | Stoltz | |
| 5,911,981 A | 6/1999 | Dahms et al. | |
| 5,914,310 A * | 6/1999 | Li et al. | 510/499 |
| 5,922,331 A | 7/1999 | Mausner | |
| 5,948,682 A | 9/1999 | Moloney | |
| 5,951,993 A | 9/1999 | Scholz et al. | |
| 5,952,392 A | 9/1999 | Katz et al. | |
| 5,961,957 A | 10/1999 | McAnalley | |
| 5,972,310 A | 10/1999 | Sachetto | |
| 5,993,846 A | 11/1999 | Friedman et al. | |
| 6,019,967 A | 2/2000 | Breton et al. | |

| | | | | | | |
|---|---|---|---|---|---|---|
| 6,033,647 | A * | 3/2000 | Touzan et al. ............... 424/45 | 2004/0197276 A1 | 10/2004 | Takase et al. |
| 6,042,848 | A | 3/2000 | Lawyer et al. | 2004/0241099 A1 | 12/2004 | Popp et al. |
| 6,045,779 | A | 4/2000 | Mueller et al. | 2004/0265240 A1 | 12/2004 | Tamarkin et al. |
| 6,087,317 | A | 7/2000 | Gee | 2005/0031547 A1 | 2/2005 | Tamarkin et al. |
| 6,090,772 | A | 7/2000 | Kaiser et al. | 2005/0054991 A1 | 3/2005 | Tobyn et al. |
| 6,093,408 | A | 7/2000 | Hasenoehrl et al. | 2005/0069566 A1 | 3/2005 | Tamarkin et al. |
| 6,110,477 | A | 8/2000 | Hernandez et al. | 2005/0074414 A1 | 4/2005 | Tamarkin et al. |
| 6,113,888 | A | 9/2000 | Castro et al. | 2005/0075407 A1 | 4/2005 | Tamarkin et al. |
| 6,116,466 | A | 9/2000 | Gueret et al. | 2005/0079139 A1 | 4/2005 | Jacques et al. |
| 6,121,210 | A | 9/2000 | Taylor | 2005/0186142 A1 | 8/2005 | Tamarkin et al. |
| 6,126,920 | A | 10/2000 | Jones et al. | 2005/0186147 A1 | 8/2005 | Tamarkin et al. |
| 6,140,355 | A | 10/2000 | Egidio | 2005/0196414 A1 | 9/2005 | Dake et al. |
| 6,146,645 | A | 11/2000 | Deckers | 2005/0205086 A1 | 9/2005 | Tamarkin et al. |
| 6,180,669 | B1 | 1/2001 | Tamarkin | 2005/0222090 A1 | 10/2005 | Cheng et al. |
| 6,183,762 | B1 | 2/2001 | Deckers | 2005/0232869 A1 | 10/2005 | Tamarkin et al. |
| 6,186,367 | B1 | 2/2001 | Harrold | 2005/0244342 A1 | 11/2005 | Friedman et al. |
| 6,187,290 | B1 | 2/2001 | Gilchrist et al. | 2005/0255048 A1 | 11/2005 | Hirsh et al. |
| 6,210,742 | B1 | 4/2001 | Deckers | 2005/0266035 A1 | 12/2005 | Healy et al. |
| 6,221,381 | B1 | 4/2001 | Shelford et al. | 2005/0271596 A1 | 12/2005 | Friedman et al. |
| 6,224,888 | B1 | 5/2001 | Vatter et al. | 2005/0271598 A1 | 12/2005 | Friedman et al. |
| 6,231,837 | B1 | 5/2001 | Stroud et al. | 2005/0281755 A1 | 12/2005 | Zarif et al. |
| 6,251,369 | B1 | 6/2001 | Stoltz | 2005/0285912 A1 | 12/2005 | Delametter et al. |
| 6,258,374 | B1 | 7/2001 | Friess et al. | 2006/0018937 A1 | 1/2006 | Friedman et al. |
| 6,287,546 | B1 | 9/2001 | Reich et al. | 2006/0018938 A1 | 1/2006 | Neubourg |
| 6,294,550 | B1 | 9/2001 | Place et al. | 2006/0029565 A1 | 2/2006 | Xu et al. |
| 6,299,900 | B1 | 10/2001 | Reed et al. | 2006/0088561 A1 | 4/2006 | Eini et al. |
| 6,306,841 | B1 | 10/2001 | Place et al. | 2006/0140984 A1 | 6/2006 | Tamarkin et al. |
| 6,328,950 | B1 | 12/2001 | Franzke et al. | 2006/0193789 A1 | 8/2006 | Tamarkin et al. |
| 6,333,362 | B1 | 12/2001 | Lorant | 2006/0222675 A1 | 10/2006 | Sabnis et al. |
| 6,358,541 | B1 | 3/2002 | Goodman | 2006/0233721 A1 | 10/2006 | Tamarkin et al. |
| 6,372,234 | B1 | 4/2002 | Deckers | 2006/0254597 A1 | 11/2006 | Thompson |
| 6,383,471 | B1 | 5/2002 | Chen et al. | 2006/0269485 A1 | 11/2006 | Friedman et al. |
| 6,395,300 | B1 | 5/2002 | Straub et al. | 2006/0272199 A1 | 12/2006 | Licciardello et al. |
| 6,410,036 | B1 | 6/2002 | De Rosa et al. | 2006/0275218 A1 | 12/2006 | Tamarkin et al. |
| 6,423,323 | B2 | 7/2002 | Neubourg | 2006/0275221 A1 | 12/2006 | Tamarkin et al. |
| 6,428,772 | B1 | 8/2002 | Singh et al. | 2007/0020304 A1 | 1/2007 | Tamarkin et al. |
| 6,433,033 | B1 | 8/2002 | Isobe | 2007/0059253 A1 | 3/2007 | Popp et al. |
| 6,468,989 | B1 | 10/2002 | Chang | 2007/0069046 A1 | 3/2007 | Eini et al. |
| 6,514,487 | B1 | 2/2003 | Barr | 2007/0142263 A1 | 6/2007 | Stahl et al. |
| 6,524,594 | B1 | 2/2003 | Santora et al. | 2007/0148112 A1 | 6/2007 | Dingley et al. |
| 6,531,118 | B1 | 3/2003 | Gonzalez et al. | 2007/0154402 A1 | 7/2007 | Trumbore et al. |
| 6,536,629 | B2 | 3/2003 | van der Heijden | 2007/0237724 A1 | 10/2007 | Abram et al. |
| 6,544,530 | B1 | 4/2003 | Friedman | 2007/0253911 A1 | 11/2007 | Tamarkin et al. |
| 6,582,710 | B2 | 6/2003 | Deckers | 2007/0280891 A1 | 12/2007 | Tamarkin et al. |
| 6,596,287 | B2 | 7/2003 | Deckers | 2007/0292355 A1 | 12/2007 | Tamarkin et al. |
| 6,599,513 | B2 | 7/2003 | Deckers | 2007/0292359 A1 | 12/2007 | Friedman et al. |
| 6,620,773 | B1 | 9/2003 | Stork et al. | 2007/0292461 A1 | 12/2007 | Tamarkin et al. |
| 6,649,574 | B2 | 11/2003 | Cardis et al. | 2008/0031908 A1 | 2/2008 | Aubrun-Sonneville et al. |
| 6,672,483 | B1 | 1/2004 | Roy | 2008/0035155 A1 | 2/2008 | Dahl |
| 6,730,288 | B1 | 5/2004 | Abram | 2008/0044444 A1 | 2/2008 | Tamarkin et al. |
| 6,753,167 | B2 | 6/2004 | Moloney | 2008/0058055 A1 | 3/2008 | LeMay et al. |
| 6,765,001 | B2 | 7/2004 | Gans et al. | 2008/0069779 A1 | 3/2008 | Tamarkin et al. |
| 6,777,591 | B1 | 8/2004 | Chaudhary | 2008/0138293 A1 | 6/2008 | Tamarkin et al. |
| 6,902,737 | B2 | 6/2005 | Quemin et al. | 2008/0138296 A1 | 6/2008 | Tamarkin et al. |
| 6,946,120 | B2 | 9/2005 | So | 2008/0152596 A1 | 6/2008 | Friedman et al. |
| 7,029,659 | B2 | 4/2006 | Abram et al. | 2008/0206155 A1 | 8/2008 | Tamarkin et al. |
| 7,137,536 | B2 | 11/2006 | Walters | 2008/0206161 A1 | 8/2008 | Tamarkin et al. |
| 2002/0032171 | A1 | 3/2002 | Chen et al. | 2008/0260655 A1 | 10/2008 | Tamarkin et al. |
| 2002/0035046 | A1 | 3/2002 | Lukenbach et al. | 2008/0292560 A1 | 11/2008 | Tamarkin et al. |
| 2002/0044659 | A1 | 4/2002 | Ohta | 2008/0299220 A1 | 12/2008 | Tamarkin et al. |
| 2002/0045659 | A1 | 4/2002 | Michelet et al. | 2009/0041680 A1 | 2/2009 | Tamarkin et al. |
| 2002/0048798 | A1 | 4/2002 | Avery et al. | 2009/0068118 A1 | 3/2009 | Eini et al. |
| 2002/0072544 | A1 | 6/2002 | Miller et al. | 2009/0130029 A1 | 5/2009 | Tamarkin et al. |
| 2002/0098215 | A1 | 7/2002 | Douin et al. | 2009/0175799 A1 | 7/2009 | Tamarkin et al. |
| 2002/0117516 | A1 | 8/2002 | Lasserre et al. | 2009/0180970 A1 | 7/2009 | Tamarkin et al. |
| 2002/0182162 | A1 | 12/2002 | Shahinpoor et al. | | | |
| 2002/0198136 | A1 | 12/2002 | Mak et al. | | FOREIGN PATENT DOCUMENTS | |
| 2003/0006193 | A1 | 1/2003 | Ikeda et al. | | | |
| 2004/0018228 | A1 * | 1/2004 | Fischell et al. .............. 424/450 | DE | 10138495 | 2/2003 |
| 2004/0053797 | A1 | 3/2004 | Chen et al. | DE | 102004016710 | 10/2005 |
| 2004/0063787 | A1 | 4/2004 | Villanueva | EP | 0156507 A1 | 10/1985 |
| 2004/0151671 | A1 | 8/2004 | Abram et al. | EP | 270 316 | 6/1988 |
| 2004/0192754 | A1 | 9/2004 | Shapira et al. | EP | 297436 | 1/1989 |

| | | |
|---|---|---|
| EP | 0404376 | 12/1990 |
| EP | 414920 | 3/1991 |
| EP | 0488089 | 6/1992 |
| EP | 0488089 A1 | 6/1992 |
| EP | 0 535 327 | 4/1993 |
| EP | 0598412 | 11/1993 |
| EP | 0598412 | 5/1994 |
| EP | 0738516 | 10/1996 |
| EP | 0824911 | 2/1998 |
| EP | 0 979 654 | 2/2000 |
| EP | 1055425 A2 | 11/2000 |
| EP | 1215258 | 6/2002 |
| EP | 1 287 813 | 3/2003 |
| EP | 1 428 521 | 6/2004 |
| EP | 1438946 | 7/2004 |
| EP | 1475381 | 11/2004 |
| FR | 2774595 | 8/1999 |
| FR | 2915891 | 11/2008 |
| GB | 808105 | 1/1959 |
| GB | 922930 | 4/1963 |
| GB | 1026831 | 4/1966 |
| GB | 1121358 | 7/1968 |
| GB | 1376649 | 12/1974 |
| GB | 1397285 | 6/1975 |
| IL | 0152486 A0 | 5/2003 |
| JP | 55069682 | 5/1980 |
| JP | 63119420 | 5/1988 |
| JP | 01100111 | 4/1989 |
| JP | 01156906 | 6/1989 |
| JP | 2255890 | 10/1990 |
| JP | 04282311 | 10/1992 |
| JP | 7215835 | 8/1995 |
| JP | 2008040899 | 2/1996 |
| JP | 8119831 | 5/1996 |
| JP | 9099553 | 4/1997 |
| JP | 10114619 | 5/1998 |
| JP | 11250543 | 9/1999 |
| JP | 2000080017 | 3/2000 |
| JP | 2000191429 | 7/2000 |
| JP | 2000351726 | 12/2000 |
| JP | 2001019606 | 1/2001 |
| JP | 2002012513 | 1/2002 |
| JP | 2002047136 | 2/2002 |
| JP | 2003055146 | 2/2003 |
| JP | 2004047136 | 2/2004 |
| JP | 2004-348277 | 12/2004 |
| JP | 2005350378 | 12/2005 |
| JP | 2006008574 | 1/2006 |
| JP | 2007131539 | 5/2007 |
| UA | 66796 | 6/2004 |
| WO | WO-86/05389 | 9/1986 |
| WO | WO-88/01863 | 3/1988 |
| WO | WO-89/06537 | 7/1989 |
| WO | WO-9005774 | 5/1990 |
| WO | WO-91/11991 | 8/1991 |
| WO | WO 91/119911 | 8/1991 |
| WO | WO-92/11839 | 7/1992 |
| WO | WO-96/03115 | 2/1996 |
| WO | WO 96/19921 | 4/1996 |
| WO | WO 96/27376 | 9/1996 |
| WO | WO-96/39119 | 12/1996 |
| WO | WO 97/39745 | 10/1997 |
| WO | WO-98/18472 | 5/1998 |
| WO | WO-98/19654 | 5/1998 |
| WO | WO-98/21955 | 5/1998 |
| WO | WO-98/23291 | 6/1998 |
| WO | WO-99/08649 | 2/1999 |
| WO | WO-99/20250 | 4/1999 |
| WO | WO-99/37282 | 7/1999 |
| WO | WO-00/09082 | 2/2000 |
| WO | WO 00/15193 | 3/2000 |
| WO | WO-00/61076 | 10/2000 |
| WO | WO-00/76461 | 12/2000 |
| WO | WO-01/08681 | 2/2001 |
| WO | WO 01/70242 A2 | 9/2001 |
| WO | WO-01/82880 | 11/2001 |
| WO | WO-02/00820 | 1/2002 |
| WO | WO-02/28435 | 4/2002 |
| WO | WO-02/41847 | 5/2002 |
| WO | WO-02/41847 A1 | 5/2002 |
| WO | WO-02/43490 | 6/2002 |
| WO | WO-02/062324 | 8/2002 |
| WO | WO 03/051294 | 6/2003 |
| WO | WO-03/051294 | 6/2003 |
| WO | WO-03/053292 | 7/2003 |
| WO | WO-03/055445 | 7/2003 |
| WO | WO-03/075851 | 9/2003 |
| WO | WO-03/092641 | 11/2003 |
| WO | WO-2004/037225 | 5/2004 |
| WO | WO-2004037225 | 5/2004 |
| WO | WO-2004/064833 A1 | 8/2004 |
| WO | WO-2004/071479 A1 | 8/2004 |
| WO | WO-2004/078896 | 9/2004 |
| WO | WO 2004/112780 A1 | 12/2004 |
| WO | WO-2005/011567 A2 | 2/2005 |
| WO | WO-2005/018530 | 3/2005 |
| WO | WO-2005/018530 A2 | 3/2005 |
| WO | WO-2005/076697 | 8/2005 |
| WO | WO-2005/097068 A1 | 10/2005 |
| WO | WO-2005097068 | 10/2005 |
| WO | WO-2005/102539 | 11/2005 |
| WO | WO-2006/003481 A2 | 1/2006 |
| WO | WO-2006/010539 | 2/2006 |
| WO | WO-2006/091229 | 8/2006 |
| WO | WO-2006/100485 | 9/2006 |
| WO | WO-2006120682 | 11/2006 |
| WO | WO-2006/129161 | 12/2006 |
| WO | WO-2006/131784 | 12/2006 |
| WO | WO-2007/039825 | 4/2007 |
| WO | WO 2007/050543 | 5/2007 |
| WO | WO-2007/054818 | 5/2007 |
| WO | WO-2007/085899 | 8/2007 |
| WO | WO-2007/085902 | 8/2007 |
| WO | WO-2007/099396 | 9/2007 |
| WO | WO-2008/008397 | 1/2008 |
| WO | WO-2008/038147 | 4/2008 |
| WO | WO-2008/075207 | 6/2008 |
| WO | WO-2008/087148 | 7/2008 |
| WO | WO-2009/069006 A2 | 6/2009 |
| WO | WO-2009/072007 A2 | 6/2009 |
| WO | WO-2009/087578 A2 | 7/2009 |
| WO | WO-2009/090495 | 7/2009 |
| WO | WO-2009/090558 A2 | 7/2009 |

OTHER PUBLICATIONS

Martindale, The extra pharmacopoeia [28th] edition, Eds.: Reynolds, J.E.F. and Prasad, A.B., The Pharmaceutical Press, London, 1982, pp. 862-864.
Wormser et al. *Letters to the Editor*, Burns, 1998, 24, 383.
Wormser et al. Arch. Toxicol., 1997, 71, 165-170.
U.S. Appl. No. 10/835,359, Tamarkin et al., Foamable Iodine Compositions, filed Apr. 28, 2004.
U.S. Appl. No. 10/911,367, Tamarkin et al., Foam Carrier Containing Amphiphilic Copolymer Gelling Agent, filed Aug. 4, 2004.
U.S. Appl. No. 10/922,555, Tamarkin et al., Foam Incorporating Eutectic Mixture, filed Aug. 20, 2004.
U.S. Appl. No. 10/922,358, Tamarkin et al., Penetrating Pharmaceutical Foam, filed Aug. 20, 2004.
Barry, B.W. et al, Comparative bio-availability and activity of proprietary topical corticosteroid preparations: vasoconstrictor assays on thirty-one ointments, British Journal of Dermatology, 93, 563-571, 1975.
Tamarkin, D., et al. Body Cavity Foam, U.S. Appl. No. 11/116,761, filed Apr. 28, 2005.

Tamarkin, D., et al. Moisturizing Foam Containing Lanolin, U.S. Appl. No. 11/099,942, filed Apr. 6, 2005.

Tamarkin, D., et al. Nonsteroidal Immunomodulating Kit and Composition and Uses Thereof, U.S. Appl. No. 11/078,902, filed Mar. 11, 2005.

Tamarkin, D., et al. Steroid Kit and Foamable Composition and Uses, U.S. Appl. No. 11/114,410, filed Apr. 26, 2005.

Tamarkin, D., et al. Vasoactive Kit and Composition and Uses Thereof, U.S. Appl. No. 11/124,676, filed May 9, 2005.

International Search Report for International Application No. PCT/IB2006/003974, Feb. 25, 2008 (3 pages).

International Search Report, International Patent Application No. PCT/IB2007/003759, Foamix Ltd., Jul. 8, 2008 (3 pages).

International Search Report, International Patent Application No. PCT/IB2007/003463, Foamix, Ltd., Jul. 18, 2008, 3 pages.

International Search Report and Written Opinion, International Application No. PCT/US2007/004459, Foamix Ltd., Dec. 9, 2008, 15 pages.

Material Safety Data Sheet, Science Lab.com, Polyethylene Glycol 1000, MSDS, Nov. 6, 2008, 6 pages.

D.W.A. Sharp Dictionary of Chemistry, Penguin Books, 1983, 3 pages.

Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.

Material Safety Data Sheet, Progesterone, Apr. 26, 2006, 5 pages.

"Licking Vaginal Dryness Without a Prescription," Estronaut, Dec. 4, 2008, 3 pages.

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Gill, A.M, et al., "Adverse Drug Reactions in a Paediatric Intensitve Care Unit," Acta Paediatr 84:438-441, 1995.

Gschnait, F., et al., "Topical Indomethacin Protects from UVB and UVA Irriadiation," Arch. Dermatol. Res. 276:131-132, 1984.

Hall, Karla, "Diaper Area Hemanglomas: A Unique Set of Concerns," http://members.tripod.com/~Michelle_G/diaper.html, Dec. 1, 2008, 8 pages.

Skin Biology, CP Serum—Copper-Peptide Serum for Skin Regeneration and Reducing Wrinkles, Skin Biology, http://web.archive.org/web/20030810230608/http://www.skinbio.com/cpserum.html, Dec. 1, 2008, 21 pages.

Galligan, John et al., "Adhesive Polyurethane Liners for Anterior Restorations," J. Dent. Res., Jul.-Aug. 1968, pp. 629-632.

Sigma-Aldrich, Material Safety Data Sheet, Hydroxyethyl Cellulose, Mar. 3, 2004, 5 pages.

International Search Report and Written Opinion, International Application No. PCT/IB2006/003628, Foamix Ltd., Dec. 7, 2007, 15 pages.

Office Action received from the U.S. Patent Office, U.S. Appl. No. 11/430,599, Jul. 28, 2008 (59 pages).

Office Action received from the U.S. Patent Office for U.S. Appl. No. 11/430,437, May 9, 2008, 55 pages.

Nicol. AIDS 2001, vol. 15, No. 14, pp. 1837-1842.

Pendergrass, Gynecol Obstet. Invest. 1996:42(3):178-82.

Hill, Randall M. (Ed.) Silicone Surfactants, Table of Contents and Chapter 7, "Silicone Surfactants: Applications in the Personal Care Industry" by David T. Floyd (30 pages).

Emulsifiers with HLB values. http://www.theherbarie.com/files/resources-center/formulating/Emulsifiers_HLB_Values.pdf accessed Aug. 5, 2009 (3 pps).

Hashim, et al. "Tinea versicolor and visceral leishmaniasis," Int J Dermatol., Apr. 1994; 33(4), pp. 258-259 (abstract only).

Hepburn, NC., "Cutaneous leishmaniasis," Clin Exp Dermatol, Jul. 2000; 25(5), pp. 363-370 (abstract only).

Hill, Randall M. (Ed.) Silicone Surfactants, Table of Contents and Chapter 7, "Silicone Surfactants: Applicants in the Personal Care Industry," by David T. Floyd, 1999 (30 Pages).

OM Cinnamate. http://www.makingcosmetics.com/sunscreens/OM-Cinnamate-p102.html accessed Sep. 26, 2009.

Savin, et al., "Tinea versicolor treated with terbinafine 1% solution," Int J. Dermatol, Nov. 1999; 38(11), pp. 863-865.

Schmidt A., "Malassezia furfur: a fungus belonging to the physiological skin flora and its relevance in skin disorders," Curtis., Jan. 1997; 59(1), pp. 21-4 (abstract).

Shear, et al., "Pharmacoeconomic analysis of topical treatments for tinea infections," Pharmacoeconomics. Mar. 1995; 7(3); pp. 251-267 (abstract only).

Sigma Aldrich, "HLB-Numbers in Lithography Nanopatterning," http://www.sigmaaldrich.com/materials-science/micro-and-nanoelectronics/lithography-nanopatterning/hlb-numbers.html, accessed: Feb. 2, 2009, pp. 1-3.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).

Benet, et al., App-lication of NMR for the Determination of HLB Values of Nonionic Surfactants, Journal of the American Oil Chemists Society, vol. 49, 1972, 499-500.

Cheshire, et al., Disorders of Sweating, www.medscape.com, Semin Neurol 23(4):399-406, 2003.

Dalby, "Determination of Drug Solubility in Aerosol Propellants," Pharmaceutical Research, vol. 8, No. 9, 1991, pp. 1206-1209.

Glaser, et al., Hyperhidrosis: A Comprehensive and Practical Approach to Patient Management, Expert Rev. Dermatol. 1(6), 773-775 (2006).

Kalkan, et al., The Measurement of Sweat Intensity Using a New Technique, Tr. J. of Medical Sciences 28, 515-517 (1998).

Kathon™ CG (product information sheet by Rohm and Haas, Jun. 2006).

Metronidazole. www.usp.org/pdf/EN/veterinary/metronidazole.pdf. accessed Sep. 10, 2009, 4 pages.

* cited by examiner

OLEAGINOUS PHARMACEUTICAL AND COSMETIC FOAM

RELATED APPLICATIONS

The invention claims priority under 35 U.S.C. §119(e) to U.S. application Ser. No. 60/530,015, filed Dec. 16, 2003, entitled "Oleaginous Pharmaceutical and Cosmetic Foam," which is incorporated by reference.

The invention claims priority under 35 U.S.C. §119(e) to U.S. application Ser. No. 60/492,385, filed Aug. 4, 2003, and entitled entitled "Cosmetic and Pharmaceutical Foam," which is incorporated by reference.

FIELD OF THE INVENTION

The invention relates to oleaginous foam compositions including cosmetic or therapeutic active agents, and methods of topical treatment using the compositions.

BACKGROUND OF THE INVENTION

Certain foam products for topical application of therapeutical agents and cosmetics have been prepared as oil-in-water emulsions. Foams and, in particular, foam compositions having a high oil content are complicated systems that do not form under all circumstances. Slight shifts in foam composition, such as the addition of an active ingredient, may destabilize the foam. It is known in the art that hydrophobic solvents are difficult to formulate into a foamproducing product. Addition of conventional hydrophobic solvents interferes with the foam forming ability of the surfactant, and thus, in the few foam products containing high-oil concentrations that have been reported, high surfactant concentrations are used, which may cause undesirable irritancy on one hand, and costly raw material usage on the other hand are used.

Oleaginous formulations for the preparation of cosmetic and therapeutic compositions are known in the art.

U.S. Pat. No. 6,620,773 relates to a foaming oil composition, which includes a surfactant mixture and an oil component, the surfactant mixture containing an anionic or zwitterionic surfactant, a nonionic surfactant and at least one ethoxylated alkyl phosphate ester component. The surfactant mixture ranges from about 15% to about 50% of the total composition, and that of the oil component ranges from about 50% to about 85%.

U.S. Pat. Nos. 5,700,396 and 5,589,515 disclose a cosmetic emulsion composition containing 0.1 to 99 wt % oily component (balance aqueous component). The oily component includes 85% or more weight % of cis $\Delta$9-octadecanoic acid or derivatives thereof, which serves as a surfactant in the formulation.

U.S. Pat. No. 6,524,594 describes a gelled oil composition containing an emulsifier, a gelling agent, an oil, and a surfactant which, when applied to the skin in the presence of water, produces a significant amount of foam. The surfactant is used in an amount from about 10% to about 20%, and more preferably, from about 15% to about 20%.

U.S. Pat. No. 6,121,210 discloses foamable, silicone oil compositions and methods of lubricating surfaces with such compositions. The compositions are oil-in-water emulsions comprising silicone oil-in-water emulsion, a liquid propellant and a foam builder comprising a solid, non-ionic lipophilic surfactant having an HLB value of about 3 to about 8. Foam stabiliziers including long claim fatty alcohols are included. A propellant is included to create a foamable composition.

In general, the foamable compositions of the art are based on oil-in-water emulsions. Furthermore, they often include a high content level of surfactants and foaming agents required to form acceptable foams which are stable and possess low specific gravity. Such surfactants, and particularly ionic surfactants, such as anionic surfactants (e.g. sodium lauryl sulfate (SDS)), may have adverse affects on certain patients, including concentration-dependent skin irritation.

There remains an unmet need for improved, stable and non-irritating oleaginous foam formulations, intended for dermal and mucosal delivery of pharmaceutical and cosmetic, with unique therapeutic and cosmetic properties.

SUMMARY OF THE INVENTION

The present invention provides stable, oleaginous foam-forming compositions including at least one active agent for dermal and mucosal delivery. The composition is dispensed as a foam providing a stable product that is pleasant and easy to spread, resulting in high patient compliance. The "oleaginous" composition has the organoleptic character of an oily substance, i.e., an oily feeling, when topically administered to the skin or mucosal tissue.

According to one aspect or the present invention, the composition includes:

a. at least one solvent selected from a hydrophobic solvent, a co-solvent, and mixtures thereof, wherein the solvent is present at a concentration of about 70% to about 96.5% by weight of the total composition;

b. a non-ionic surface-active agent at a concentration of about 0.1% to less than about 10% by weight of the total composition;

c. at least one gelling agent at a concentration of about 0.1% to about 5% by weight of the total composition;

d. at least one active agent in a therapeutically effective concentration; and e. at least one liquefied or compressed gas propellant, at a concentration of about 3% to about 25% by weight of the total composition.

Water and optional ingredients are added to complete the total weight to 100%, although the composition may be essentially free of lower alkyl alcohols. In one or more embodiments, the oleaginous composition of the present invention contains less than about 5% of a lower alcohol having up to 5 carbon atoms in its carbon chain skeleton.

In one or more embodiments, the oleaginous composition includes water at a concentration less than about 30%, preferably less than about 20%, more preferably less than about 10% by weight.

In one or more embodiments, the oleaginous composition of the present invention further includes a foam adjuvant.

In yet other embodiments, the oleaginous composition of the present invention forms an emulsion.

In one or more embodiments, the oleaginous composition of the present invention includes a hydrophobic solvent having solubility in distilled water at ambient temperature of less than about one gram per 100 ml. The hydrophobic solvent may be a mineral oil, MCT oil, triglyceride oil, silicone oil, a polyunsaturated oil, an unsaturated oil and an essential oil, and mixtures thereof.

In one or more embodiments, the at least one solvent is a co-solvent. In one or more embodiments, the co-solvent is a polyethylene glycol derivative, or glycerin. In one or more embodiments, the oleaginous composition of the present invention includes a mixture of at least one hydrophobic solvent and at least one co-solvent. The mixture of at least one hydrophobic solvent and the at least one co-solvent may have a weight ratio of about 1:8 to about 8:1. In one or more embodiments, a mixture of at least one hydrophobic solvent and glycerin is used; and the mixture may have a weight ratio of about 1:4 to about 4:1, or about 1:2 to about 2:1.

According to one or more embodiments, the composition includes at least one solvent having a high solubilization capacity, termed herein a "potent solvent". In the context of the present invention, a potent solvent is other than mineral oil and solubilizes a specific active agent substantially better than a hydrocarbon solvent such as mineral oil or petrolatum, for example, 5-fold better than mineral oil; or even 10-fold better than mineral oil.

In one or more embodiments, the oleaginous composition of the present invention contains a potent solvent selected from the group consisting of polyethylene glycol, propylene glycol, hexylene glycol, butanediols and isomers thereof, glycerol, benzyl alcohol, DMSO, ethyl oleate, ethyl caprylate, diisopropyl adipate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol).

In one or more embodiments, the surface-active agent is a non-ionic surfactant and can be, for example, a phospholipid. The surface-active agent can be a mixture of at least one non-ionic surfactant and at least one ionic surfactant, for example, at a weight ratio of about 20:1 to about 1:1.

In one or more embodiments, the composition includes at least one gelling agent selected from the group consisting of natural polymeric materials, semi-synthetic polymeric materials, synthetic polymeric materials, inorganic gelling agents and mixtures thereof.

The oleaginous composition of the present invention upon extrusion from a pressured container has a specific gravity of about 0.02 gr/ml to about 0.5 gr/mL, and is useful for treating, alleviating or preventing a dermatological or mucosal disorder.

According to a further aspect of the present invention, an oleaginous water-in-oil emulsion is provided. The emulsion can be essentially free of lower alkyl alcohols. The emulsion includes:

at least one solvent selected from a hydrophobic solvent, a co-solvent and an emollient at a concentration of about 30% to about 96.5% by weight;

water;

at least one non-ionic lipophilic surface acting agent having an HLB value of about 3 to about 10 at a concentration of about 0.1% to less than about 10% by weight, at least one gelling agent at a concentration of about 0.1% to about 5% by weight.

at least one active agent at a therapeutically effective concentration; and at least one liquefied or compressed gas propellant at a concentration of about 3% to about 25% by weight of the total composition.

In one or more embodiments, the oleaginous emulsion of the present invention contains less than about 5% of a lower alcohol having up to 5 carbon atoms in its carbon chain skeleton. In another embodiment the oleaginous composition of the present invention further comprises a foam adjuvant.

In one or more embodiments, the oleaginous water-in-oil emulsion contains a hydrophobic solvent and water at a weight ratio of about 1:3 to about 6:1.

In one or more embodiments, the oleaginous emulsion contains a hydrophobic solvent having solubility in distilled water at ambient temperature of less than about one gram per 100 ml. The hydrophobic solvent may be selected from mineral oil, MCT oil, triglyceride oil, silicone oil, a polyunsaturated oil, an unsaturated oil and an essential oil.

The oleaginous emulsion may include a potent solvent selected from a hydrophobic solvent other than mineral oil, a co-solvent and an emollient, wherein the potent solvent solubilizes the active agent substantially better than mineral oil solubilizes the active agent, e.g at least 5-fold better or at least 10-fold better than mineral oil solubilizes the active agent.

In one or more embodiments, the oleaginous emulsion contains a surface-active agent having a HLB value in the range of about 3 to about 10, which promote the formation of a water-in-oil emulsion.

In one or more embodiments, the oleaginous emulsions contains at least one gelling agent selected from the group consising of natural polymeric materials, semi-synthetic polymeric materials, synthetic polymeric materials, inorganic gelling agents and mixtures thereof.

The active agent can be a therapeutic agent or a cosmetic agent. The therapeutic agent is selected for the treatment or prophylaxis of a disorder of the skin, mucosal membrane, ear channel, vagina, penile urethra and rectum. In one embodiment therapeutic agent is selected from an anti-infective, an antibiotic, an antibacterial agent, an antifungal agent, an antiviral agent, an antiparasitic agent, an antiinflammatory agent, an anesthetic, an analgesic, an antiallergic agent, a corticosteroid, a retinoid, an antiproliferative agent, an anticancer agent, a photodynamic therapy agent, a lubricating agent and mixtures thereof.

Alternatively, the active agent is an inorganic solid matter, preferably a metal oxide, more preferably zinc oxide.

The active agent can also be a cosmetic agent such as a retinoid, an anti-wrinkle agent, a radical scavenger, a self-tanning agent, a skin whitening agent a skin protective agent, an anti-cellulite agent, a massaging oil and an anti-wart agent.

In another aspect, the present invention provides a method of treating, alleviating or preventing a dermatological or mucosal disease or disorder, comprising administering topically to a subject having the disease or disorder a therapeutically effective amount of the oleaginous compositions or the oleaginous water-in-oil emulsions of the present invention.

In yet another aspect, the present invention also provides a method of designing a foamable composition, containing at least one active agent that is substantially insoluble in a hydrocarbon solvent including mineral oil. The method includes selecting at least one active agent, and identifying a solvent that solubilizes the active agent substantially better than mineral oil solubilizes the active agent. The method may further comprisie the step of adjusting the type and concentration of surfactant and gelling agent to provide a foamable composition.

In one or more embodiments, the potent solvent solubilizes the active agent 5-fold better or even 10-fold better than mineral oil solubilizes the active agent.

DETAILED DESCRIPTION OF THE INVENTION

Despite the commonly known fact that hydrophobic solvents, and oils in particular, are difficult to formulate into foam-producing products and that addition of conventional hydrophobic solvents interferes with the foam forming ability of the surfactant, the present invention has surprisingly discovered stable oleaginous foam compositions, comprising at least one active agent for dermal and mucosal delivery. The compositions are dispensed as a foam providing a stable product that is pleasant and easy to use for high patient and consumer compliance. The at least one active agent is selected from a therapeutically active agent or a cosmetic agent.

Surprisingly, the compositions of the present invention require low surfactant concentrations, e.g., less than 10% by weight and often much less, thus preventing both undesirable irritancy and costly raw material usage.

According to one aspect of the present invention, the foamable compositions are light weight, have low density, spread easily and comfortably over large body area, and are thus, economical.

The compositions of the present invention comprise at least one solvent selected from a hydrophobic solvent, a co-solvent, an emollient and mixtures thereof, which provides a refatting and skin soothing effect. The selected solvents allow the inclusion of oil-soluble active agents in the formulation. In one or more embodiments, the solvents provide synergistic benefits in combination with the active agent. The compositions may comprise at least one oil soluble active agent.

In one or more embodiments, the compositions require only low concentrations of a foaming agent in order to generate a stable foam. The reduced surfactant requirement is advantageous since surfactants are known to be irritating when in contact with the skin at elevated concentrations.

The compositions are easily spreadable, allowing treatment of large areas such as the arms, back, trunk, legs and the breast. Furthermore, due to flow properties, they spread effectively into folds and wrinkles and absorb into the skin, providing uniform distribution of the active agent without the need of extensive rubbing thus providing a unique means for the treatment of large body areas.

The compositions may be used for the treatment of body cavities, such as the vagina, penile urethra, rectum and the ear channel due to their expansion properties.

Class A Foam Composition

According to one aspect the present invention provides an oleaginous foam composition for topical application including:

at least one solvent selected from a hydrophobic solvent, a co-solvent, an emollient and mixtures thereof, at a concentration of about 70% to about 96.5% by weight, at least a non-ionic surface active agent at a concentration of about 0.1% to less than about 10% by weight and, optionally, having an HLB value of about 9 or less;

at least one gelling agent at a concentration of about 0.1% to about 5% by weight;

at least one active agent at a therapeutically effective concentration; and a liquefied or compressed gas propellant at a concentration of about 3% to about 25% by weight of the total composition.

The balance of the composition contains water and additional optional components. The content of the foam composition is presented herein as concentration (percent by weight, % w/w). The foam composition can be a homogeneous mixture or an emulsion. confirm that this is true for the Class A foams.

Such a composition is placed in a pressurized aerosol container and, upon release from the container, creates a novel therapeutically-beneficial foam product.

Low water content is important in order to attain high skin and body tissue lubrication, refatting, occlusive effects and effective skin absorption of a active agents. It is also important in order to avoid degradation of water sensitive active agents.

Thus, in one or more embodiments, the composition comprises water at a concentration of about 30% or less, or at a concentration less than about 20%, or at a concentration less than about 10% by weight.

The composition is optionally substantially free of short chain alcohols, i.e. comprises less than about 5% by weight of a short chain alcohol having 5 or less carbon atom in its skeleton, and may further comprise a foam adjuvant.

According to one embodiment, the composition comprises a solvent selected from a hydrophobic solvent and an emollient and at least one co-solvent. According to one embodiment the co-solvent is a hydrophilic solvent, other than a short chaim alcohol, selected from an organic solvent that dissolves in water. Non-limiting examples of such co-solvents include propylene glycol, glycerol, and other poly-hydroxy solvents. Preferably, the composition comprises glycerol as co-solvent. In one embodiment the composition comprises a hydrophobic solvent component and a co-solvent at a weight ratio in the range of about 4:1 and about 1:4, or about 2:1 to 1:2. In an even further embodiment of the present invention, the co-solvent constitutes a continuous phase of the emulsion and a minor portion of water is included in the co-solvent phase.

Such a composition is placed in an aerosol container and, upon release from the aerosol container, creates a therapeutically-beneficial foam product.

Class B Foam Composition:

According to another aspect the present invention provides an oleaginous foam composition comprising water-in-oil emulsion, i.e., an emulsion having one phase comprising at least one hydrophobic component (oil phase) and one phase which comprises water. Due to the fact that the continuous phase of the emulsion is the oil phase, the composition provides oily feeling, occlusive properties and protective effects. Notably, while it is known that a composition with a continuous oil phase is unlikely to form foam without high amounts of surfactants, the composition of the present invention surprisingly forms a stable foam with low density. In one or more embodiments, there is an overlap between the compositions of Class A and Class B, the distinction being that Class B compositions are formed as water-in-oil emulsions.

According to one embodiment, the water-in-oil emulsion composition contains:

at least one solvent selected from a hydrophobic solvent, a co-solvent, an emollient and mixtures thereof, at a concentration of about 30% to about 96% by weight, water at a concentration of 1% to about 70% by weight;

at least one non-ionic lipophilic surface active agent, preferably having an HLB value of about 3 to about 10, more preferably about 3.5 to about 9 at a concentration of about 0.1% to about 10% by weight, or between about 0.1% and about 5% by weight, ore even between abour 0.1% and about 2% by weight;

at least one gelling agent at a concentration of about 0.1% to about 5% by weight;

at least one active agent at a therapeutically effective concentration; and a liquefied or compressed gas propellant at a concentration of about 3% to about 25% by weight of the total composition, in an aerosol container.

According to a further embodiment, the ratio between the oil phase and water is between about 1:3 and about 6:1.

The term "oleaginous" is defined as "having the nature or qualities of oil". The terms "oleaginous composition", "oleaginous foam" and "oleaginous foamable composition" as used herein interchangeably refer to a composition that has the organoleptic character of an oily substance, i.e., oily feeling, when topically administered to a body area, such as the skin or mucosal tissue.

In the context of the present invention, an oleaginous foam is a composition comprising at least one solvent selected from a hydrophobic solvent, a co-solvent, an emollient and mixtures thereof in the continuous phase of the composition and is characterized by an oily feeling upon application to a body surface.

Such an oleaginous composition may provide an enhanced occlusive effect, which may in turn control the drug residence time and skin penetration of an active agent. Furthermore, oleaginous compositions provide moisturizing effects, refatting effects, protective effects and lubrication which contribute to the treatment of dermatological disorders. Thus, a composition of this nature, comprising an oleaginous vehicle and an active agent is expected to provide a synergistic therapeutic effect.

Solvents

The at least one solvent of the composition of the present invention is selected from a hydrophobic solvent, an emollient, a silicone oil, a co-solvent, and a mixture thereof. The solvent occupies at least the continuous phase; however, it may also partition into the discontinuous phase in those instances when the composition is an emulsion.

Hydrophobic Solvent

A "hydrophobic solvent" as used herein refers to a material having solubility in distilled water at ambient temperature of less than about 1 gm per 100 mL, or less than about 0.5 gm per 100 mL, or even less than about 0.1 gm per 100 mL. It is liquid at ambient temperature.

In one preferred embodiment, the at least one solvent is a hydrophobic solvent such as mineral oil. Mineral oil (Chemical Abstracts Service Registry number 8012-95-1) is a mixture of aliphatic, naphthalenic, and aromatic liquid hydrocarbons that derive from petroleum. They are typically liquid, their viscosity is in the range of between about 35 CST and about 100 CST (at 40° C.), and their pour point (the lowest temperature at which an oil can be handled without excessive amounts of wax crystals forming so preventing flow) is below 0° C. By contrast, white petrolatum, also termed "Vaseline", is disadvantageous, due to its waxy nature and semi-solid texture. It is known to leave a waxy and sticky feeling after application and occasionally stain cloths. Thus, white petrolatum as well as other wax-like, semi-solid compounds are undesirable as a hydrophobic solvent according to the present invention.

According to one embodiment the oleaginous foam composition of the present invention comprises at least one solvent that is a hydrophobic solvent selected from mineral oil, a triglyceride oil, an ester of a fatty acid, an ester of a dicarboxylic acid, silicone oil, a polyunsaturated oil, an unsaturated oil and an essential oil.

According to one embodiment, preferred hydrophobic solvents are liquid oils originating from vegetable, marine or animal sources. The hydrophobic solvent may be selected from a saturated or an unsaturated oil. By way of example, the unsaturated oil may be selected from the group consisting of olive, corn, soybean, canola, cottonseed, coconut, sesame, sunflower, borage seed, syzigium aromaticum, hempseed, herring, cod-liver, salmon, flaxseed, wheat germ and evening primrose oils and mixtures thereof, at any proportion.

One class of hydrophobic solvents includes polyunsaturated oils, containing omega-3 and omega-6 fatty acids, which are know to possess therapeutic properties thorugh different modes of action. Examples of such polyunsaturated fatty acids are linoleic and linolenic acid, gamma-linoleic acid (GLA), eicosapentaenoic acid (EPA) and docosahexaenoic acid (DHA). Thus, in one preferred embodiment of the present invention the at least one hydrophobic solvent comprises at least 6% of an oil selected from omega-3 oil, omega-6 oil, and mixtures thereof.

Another preferred class of hydrophobic solvents comprises the essential oils, which are considered "therapeutic oils", which contain active biologically occurring molecules and, upon topical application, exert a therapeutic effect. Examples of such oils are rosehip oil, which contain retinoids and is known to reduce acne and post-acne scars, tea tree oil, which possesses anti-microbial activity including antibacterial, antifungal and antiviral properties. Other examples of essential oils are basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla, verbena, as well as any other therapeutically beneficial oil known in the art of herbal medication.

Emollient

A further preferred class of solvents are "emollients" that have a softening, refatting, or soothing effect, especially when applied to body areas, such as the skin and mucosal surfaces. Emollients are not necessarily hydrophobic. Without derogating the generality of this definition, examples of suitable emollients for use include hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, sucrose esters of fatty acids, octyl hydroxystearate and mixtures thereof. Examples of other suitable emollients may be found in the Cosmetic Bench Reference, pp. 1.19-1.22 (1996).

Silicone Oil

According to the present invention, silicone oils are particularly preferred solvents, due to their known skin protective and occlusive properties. Suitable silicone oils or fluids for use in the invention may be selected from non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers. These are preferably chosen from cyclic or linear polydimethylsiloxanes containing from about 3 to about 9, preferably from about 4 to about 5, silicon atoms. Volatile silicones such as cyclomethicones can also be used. Water-soluble silicones, such as dimethicone copolyol are not included in the definition of silicone oils (as hydrophobic solvents) according to the present invention. In one or more embodiments, the at least one solvent comprises at least 2% silicone oil, or at least 5% silicone oil.

Co-solvent

A "co-solvent" is an organic solvent, other than a short chain alcohol, typically soluble in both water and oil. Examples of co-solvents, according to the present invention include: polyols, such as glycerol (glycerin), propylene glycol, hexylene glycol, diethylene glycol, propylene glycol n-alkanols, terpenes, di-terpenes, tri-terpenes, terpen-ols, limonene, terpeneol, 1-menthol, dioxolane, ethylene glycol, other glycols, sulfoxides, such as dimethylsulfoxide (DMSO), dimethylformanide, methyl dodecyl sulfoxide, dimethylacetamide; monooleate of ethoxylated glycerides (with 8 to 10 ethylene oxide units); azone (1-dodecylazacycloheptan-2-one), 2-(n-nonyl)-1,3-dioxolane; esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one preferred embodiment the co-solvent is a polyethylene glycol (PEG) or PEG derivative that is liquid at ambient temperature, including PEG200 (MW about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

In one or more preferred embodiments, the at least one solvent comprises a mixture (e.g., an emulsion) of a hydrophobic solvent and glycerin, as described, for example, in U.S. Pat. No. 6,544,530 to Friedman. The ratio of hydrophobic solvent to glycerin can range from about 1:4 to about 4:1, and more preferably from about 1:2 to about 2:1.

In several cases, a given solvent can be defined as both emollient and co-solvent.

Potent Solvent

In one or more embodiments of the present invention, the foamable composition includes a potent solvent, in addition to or in place of one of the hydrophobic solvents, co-solvents and emollients of the composition. A potent solvent is a solvent other than mineral oil that solubilizes a specific active agent substantially better than a hydrocarbon solvent such as mineral oil or petrolatum. For example, a potent solvent solubilizes the active agent 5 fold better than a hydrocarbon solvent; or even solubilizes the active agent 10-fold better than a hydrocarbon solvent.

In one or more embodiments of the present invention, the composition includes at least one active agent in a therapeutically effective concentration; and at least one potent solvent in a sufficient amount to substantially solubilize the at least one active agent in the composition. The term "substantially soluble" means that at least 95% of the active agent has been solubilized, i.e., 5% or less of the active agent is present in a solid state. In one or more embodiments, the concentration of the at least one potent solvent is more than about 40% of the at least one solvent of the composition of the present invention; or even more than about 60%.

Non-limiting examples of pairs of active agent and potent solvent include:

Betamethasone valerate: Practically insoluble in mineral oil (<0.01%); soluble more than 1% in glycofurol.

Hydrocortisone butyrate: Practically insoluble in mineral oil (<0.01%); soluble more than 1% in glycofurol.

Metronidazole: Practically insoluble in mineral oil (<0.01%); soluble more than 1% in dimethyl isosrbide.

Ketoconazole: Practically insoluble in mineral oil (<0.01%); soluble more than 1% in glycofurol, propylene glycol and dimethyl isosrbide.

Mupirocin: Practically insoluble in mineral oil (<0.01%); soluble more than 1% in glycofurol, hexylene glycol, dimethyl isosorbide, propylene glycol and polyethylene glycol 400 (PEG 400).

Meloxicam, a nonsteroidal anti-inflammatory agent: Practically insoluble in mineral oil (<0.001%); soluble in propylene glycol: 0.3 mg/mL; and in PEG 400: 3.7 mg/mL.

Progesterone: Practically insoluble in mineral oil (<0.001%); soluble in PEG 400: 15.3 mg/mL.

A non-limiting exemplary list of solvents that can be considered as potent solvents includes polyethylene glycol, propylene glycol, hexylene glycol, butanediols and isomers thereof, glycerol, benzyl alcohol, DMSO, ethyl oleate, ethyl caprylate, diisopropyl adipate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol).

In another aspect, the present invention provides a method of designing a stable oleaginous foamable composition by selecting at least one active agent; and identifying a solvent that solubilizes the active agent substantially better than mineral oil or petrolatum, for example, solubilizes the active agent 5-fold better or even 10-fold better than a hydrocarbon solvent such as mineral oil or petrolatum. The method may further include adjusting the type and concentration of surfactant and gelling agent to provide a foamable composition.

The use of a potent solvent in a foam composition provides an improved method of delivering poorly soluble therapeutic agents to a target area. It is known that low drug solubility results in poor bioavailability, leading to decreased effectiveness of treatment. Foam compositions of the present invention, for which the solvent includes a potent solvent, increase the levels of the active agent in solution and thus, provde high delivery and improved therapy.

Potent solvents, as defined herein, are usually liquid. Formulations comprising potent solvents and active agents are generally disadvantageous as therapeutics, since their usage involves unwanted dripping and inconvenient method of application; resulting in inadequate dosing. Surprisingly, the foams of the present invention, which are drip-free, provide a superior vehicle for such active agents, enabling convenient usage and accurate effective dosing.

The at least one solvent of the present invention may include a mixture of the above solvents selected from the group of hydrophobic solvents, silicone oils, emollients co-solvents and potent solvents in any proportion.

Surface-active Agents

Surface-active agents (surfactants) may include an agent that has a property selected from linking oil and water in the composition, in the form of an emulsion, and evolving a foam. A surfactant's hydrophilic/lipophilic balance (HLB) describes the emulsifier's affinity towards water or oil. The HLB scale ranges from about 1 (totally lipophilic) to 45 (totally hydrophlic) and in the case of non-ionic surfactants from 1 to 20 totally hydrophlic), with 10 representing an equal balance of of both hydrophilic and lipophilic characteristics. Lipophilic emulsifiers from water-in-oil (w/o) emulsions, hydrophilic surfactants form oil-in-water (o/w) emulsions. The HLB of a blend of two emulsifiers equals the weight fraction of emulsifier A times its HLB value, plus the weight fraction of emulsifier B times its HLB value. (weighted average).

Without wishing to be bound by any particular theory or mode of operation, hydrophilic surfactants produce oil-in-water (o/w) microemulsions, whereas lipophilic surfactants are used to promote emulsification of the aqueous phase into the oil phase.

The composition of the present invention according to one or more embodiments includes at least one surface active agent or surfactant, which is intended to both stabilize the formulation and to evolve an acceptable foam.

A composition having a low concentration of an ionic surfactant is important in terms of safety, since high concentrations of surfactants are known to evolve skin and mucosal membrane irritation. Unlike certain foamable oleaginous compositions of the art, the total surfactant employed to obtain foam that is stable, of low specific gravity and has a fine bubble structure is relatively low. Low surfactant levels, particularly of ionic surfactants, are preferred to reduce skin irritations. The composition of the present invention comprises total surfactant in the range of about 0.1% to less than about 10% of the foamable composition, and is typically less than about 5%, or even less than about 2%.

According to one or more embodiments the at least one surfactant is selected from hydrophilic, hydrophobic, and a mixture of hydrophilic and hydrophobic surfactants. As is well known in the art, the terms "hydrophilic" and "hydrophobic" are relative terms. A combination of surface-active agents is possible.

According to one or more embodiments, suitable surfactants for formation of a water-in-oil emulsion have an HLB value of no greater than 10, preferably from about 3 to about 9. Thus, the composition may include a single surface-active agent having an HLB value between 3 and 9, or a mixture of surface-active agents having a weighted average of their HLB values between 3 and 9.

Suitable water-in-oil emulsifiers include, but are not limited to, sorbitan derivatives such as sorbitan laurate and sorbitan palmitate; alkoxylated alcohols such as laureth-4; hydroxylated derivatives of polymeric silicones, such as dimethicone copolyol; alkylated derivatives of hydroxylated polymeric silicones, such as cetyl dimethicone copolyol; glyceryl esters such as polyglyceryl-4 isostearate; beeswax derivatives such as sodium isostearoyl-2-lactylate; lecithin; and mixtures thereof. In conjunction with the oil component being a silicone oil, the preferred emulsifiers are hydroxylated derivatives of polymeric silicones and alkylated derivatives thereof.

According to one or more embodiments the present invention, the composition comprises at least one non-ionic surfactant. In one or more embodiments, the composition includes at least one non-ionic surfactant and at least one ionic surfactant selected from the group of anionic, cationic, zwitterionic, at a weight ratio of between about 1:1 and about 20:0.1, or preferably at a weight ratio of about 4:0.1 to about 20:0.1.

The choice of specific surfactants should be made keeping in mind the particular hydrophobic therapeutic agent to be used in the composition, and the range of polarity appropriate for the chosen therapeutic agent. With these general principles in mind, a very broad range of surfactants is suitable for use in the present invention.

Additional non-limiting examples of possible surfactants include polysorbates, such as polyoxyethylene (20) sorbitan monostearate (Tween 60) and polyoxyethylene (20) sorbitan monooleate (Tween 80); Polyoxyethylene (POE) fatty acid esters, such as Myrj 45, Myrj 49 and Myrj 59; poly(oxyethylene) alkylyl ethers, such as poly(oxyethylene) cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; fatty alcohols or acids, mono or diglycerides, isoceteth-20, sodium methyl cocoyl taurate, sodium methyl oleoyl taurate, sodium lauryl sulfate, triethanolamine lauryl sulfate and betaines, provided that, in the case of a single surfactant, the HLB value is between 3 and 9; and in the case of a mixture of surface-active agents, the weighted average of their HLB values is between 3 and 9.

In one or more embodiments, the at least one surface active agent is a phospholipid. In a one or more embodiments, the phospholipid is phosphatidylcholine or 1,2-diacyl-sn-glycerol-3-phosphorylcholine, also termed "lecithin", which is a naturally occuring phospholipid which possesses surfactant properties. Lecithin is the most abundant lipid in the membranes of biological tissues and as such, is considered a non-irritant. Lethicin is a phospholipid composition very similar in composition to that of human skin. For this reason, it is possible to use lethicin as an emulsifier or a surfact-active agent at levels about 10% by weight. In one or more embodiments, the surface-active agent includes lethicin up to about 10% by weight and the total surfact-active agent (when a mixture of agents is used) can be up to 15% by weight.

A composition having a low concentration of an ionic surfactant, preferably no ionic surfactant, is important in terms of safety, since high concentrations of surfactants are known to evolve skin irritation.

Gelling Agents

The composition according to one or more embodiments of the present invention include at least one gelling agent at a concentration of about 0.1% to about 5%. The at least one gelling agent is selected from a natural polymeric material, a semi-synthetic polymeric material, a synthetic polymeric material, an inorganic gelling agent and mixtures thereof.

Exemplary gelling agents that can be used in accordance with one or more embodiments of the present invention include for example, but are not limited to, naturally-occurring polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Mixtures of the above compounds are contemplated.

Further exemplary gelling agents include the acrylic acid/ethyl acrylate copolymers and the carboxyvinyl polymers sold, for example, by the B.F. Goodrich Company under the trademark of Carbopol® resins. These resins consist essentially of a colloidal water-soluble polyalkenyl polyether crosslinked polymer of acrylic acid crosslinked with from 0.75% to 2% of a crosslinking agent such as polyallyl sucrose or polyallyl pentaerythritol. Examples include Carbopol® 934, Carbopol® 940, Carbopol® 950, Carbopol® 980, Carbopol® 951 and Carbopol® 981. Carbopol® 934 is a water-soluble polymer of acrylic acid crosslinked with about 1% of a polyallyl ether of sucrose having an average of about 5.8 allyl groups for each sucrose molecule.

Yet, another preferred group of gelling agents includes inorganic gelling agents, such as silicone dioxide (fumed silica) including but not limited to AEROSIL 200 (DEGUSSA).

The at least one gelling agent is present in an amount in the range of about 0.1% to about 5.0 wt % of the foamable composition. In one or more embodiments, it is typically less than 1 wt % of the foamable composition.

Foam Adjuvants

The composition of the present invention may optionally further include at least one foam adjuvant. In one or more embodiments, foam adjuvants include fatty alcohols having 15 or more carbons in their carbon chain, such as cetyl alcohol and stearyl alcohol (or mixtures thereof). Other examples of fatty alcohols are oleyl alcohol (C18, unsaturated), arachidyl alcohol (C20), behenyl alcohol (C22), 1-triacontanol (C30), as well as alcohols with longer carbon chains (up to C50). The concentration of the fatty alcohol that is required to support the foam system is inversely related to the length of its carbon chains. Fatty alcohols derived from beeswax including a mixture of alcohols, a majority of which has at least 20 carbon atoms in their carbon chain, are especially well suited as foam adjuvants according to the present invention.

Another class of foam adjuvants, according to one or more embodiments of the present invention, includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof.

Optionally, the carbon atom chain of the fatty alcohol or the fatty acid may have at least one double bond. A further class of foam adjuvant according to the present invention comprises a long chain fatty alcohol or fatty acid, wherein the carbon atom chain is branched. In an additional preferred class of foam adjuvants, the carbon chain of said fatty acid is substituted with a hydroxyl group, such as 12-hydroxy stearic acid.

The foam adjuvant according to the present invention may comprise a mixture of fatty alcohols, fatty acids and hydroxy fatty acids and derivatives thereof in any proportion, providing that the total concentration is about 0.1% to about 10% (w/w) preferably about 0.1% to about 5% (w/w) in one or more embodiments, the total concentration is about 0.4% to about 2.5% (w/w) of the total composition.

A feature of fatty alcohols and fatty acids relevant to their use in the foamable compositions according to one or more embodiments of the present invention is related to their therapeutic properties per se. Long chain saturated and mono unsaturated fatty alcohols, e.g., stearyl alcohol, erycyl alcohol, arachidyl alcohol and docosanol have been reported to possess antiviral, anti infective, anti-proliferative and anti-inflammatory properties (U.S. Pat. No. 4,874,794). Longer chain fatty alcohols, e.g., tetracosanol, hexacosanol, heptacosanol, octacosanol, triacontanol, etc. are also known for their metabolism modifying properties and tissue energizing properties. Long chain fatty acids have also been reported to possess anti-infective characteristics. Thus, the pharmaceutical or cosmetic composition of the present invention, comprising the optional foam adjuvant provides an extra or added therapeutic benefit.

Water Content

The creation of a foamable composition with low water content is not easy, and usually requires very high concentrations of a foaming surfactant system, which may comprise a high proportion of ionic surfactants. However, ionic surfactants are known to be skin irritants in a concentration-dependent manner, and thus, their use in the treatment of sensitive skin and other body tissues is very limited. Surprisingly, the compositions of the present invention have a low water content, and yet require very low concentration of surfactants, which are primarily non-ionic.

Substantially Alcohol Free

Lower alcohols, having up to 5 carbon atoms in their carbon chain skeleton, such as ethanol, propanol, isopropanol, butanol, iso-butanol, t-butanol and pentanol are considered less desirable solvents or co-solvents due to their skin-irritating effect. Thus, the composition of the present invention is substantially alcohol-free and should comprise less than about 5% final concentration of lower alcohols, preferably less than 2%, more preferably less than 1%.

Optional Ingredients

The pharmaceutical or cosmetic composition of the present invention may further optionally comprise a variety of therapeutic or cosmetic ingredients, which are added in order to fine-tune the consistency of the formulation, protect the formulation components from degradation and oxidation and bestow their cosmetic acceptability. Such excipients may be selected, for example, from the group consisting of diglycerides, triglycerides, stabilizing agents, antioxidants, glycerol, flavoring, colorant and odorant agents and other formulation components, used in the art of pharmaceutical and cosmetic formulary. A pharmaceutical or cosmetic composition manufactured according to the present invention is very easy to use. When applied onto the afflicted body surface of humans or animals, it is in a foam state, allowing free application without drip or spillage. Upon further application of a mechanical force, e.g., by rubbing the composition onto the body surface, it freely spreads on the surface and is rapidly absorbed.

Active Agents

It is to be understood that the active agents useful herein can in some instances provide more than one benefit or operate via more than one mode of action. Therefore, classifications herein are made for the sake of convenience and are not intended to limit the active agent to that particular application or applications listed.

The composition of the present invention comprises at least one active agent that provides therapeutic or cosmetic activity.

The composition of the present invention comprising at least one "active agent", provides the following benefits:

favorable spreadability and absorption, compared to conventional ointment, cream, lotion and the like; improved treatment convenience, leading to better compliance;

enhanced delivery, leading to elevated bioavailability of the drug or cosmetic active agent in the target organ, thereby improving treatment efficacy.

In the context of the present invention, pharmaceutical and cosmetic active agents are included under the definition of at least one active agent. According to one embodiment the at least one active agent may be a single agent or a combination of agents that can be dissolved in the oleaginous carrier composition.

According to one embodiment, the at least one active agent is a hydrophobic agent, having solubility in distilled water at ambient temperature of less than about 1 gm per 100 mL, more preferable less than about 0.5 gm per 100 mL, and most preferably less than about 0.1 gm per 100 mL. In another embodiment, the at least one active agent is any therapeutic or cosmetic agent, providing that it is encapsulated in a hydrophobic envelope.

In another embodiment, the at least one active agent is insoluble and thus, incorporated in the foamable carrier of the present invention by suspension.

Non-limiting examples of active agents include antibiotic, antibacterial, antifungal, antiviral, antiinflammatory, anesthetic, analgesic, antiallergic, corticosteroid, retinoidretinoids, lubricating agents and antiproliferative medications and mixtures thereof at any proportion. The concentration of said agents may be adopted to exert a therapeutic effect on a disease when applied to an afflicted area.

A general non-limiting list of hydrophobic active agents include abacavir, acebutolol, acrivastine, alatrofloxacin, albuterol, albendazole, alprazolam, alprenolol, amantadine, amiloride, aminoglutethimide, amiodarone, amitriptyline, amlodipine, amodiaquine, amoxapine, amphetamine, amphotericin, amprenavir, amrinone, amsacrine, astemizole, atenolol, atropine, azathioprine, azelastine, azithromycin, baclofen, benethamine, benidipine, benzhexol, benznidazole, benztropine, biperiden, bisacodyl, bisanthrene, bromazepam, bromocriptine, bromperidol, brompheniramine, brotizolam, bupropion, butenafine, butoconazole, cambendazole, camptothecin, carbinoxamine, cephadrine, cephalexin, cetrizine, cinnarizine, chlorambucil, chlorpheniramine, chlorproguanil, chlordiazepoxide, chlorpromazine, chlorprothixene, chloroquine, cimetidine, ciprofloxacin, cisapride, citalopram, clarithromycin, clemastine, clemizole, clenbuterol, clofazimine, clomiphene, clonazepam, clopidogrel, clozapine, clotiazepam, clotrimazole, codeine, cyclizine, cyproheptadine, dacarbazine, darodipine, decoquinate, delavirdine, demeclocycline, dexamphetamine, dexchlorpheniramine, dexfenfluramine, diamorphine, diazepam, diethylpropion, dihydrocodeine, dihydroergotamine, diltiazem, dimenhydrinate, diphenhydramine, diphenoxylate, diphenylimidazole, diphenylpyraline, dipyridamole, dirithromycin, disopyramide, dolasetron, domperidone, donepezil, doxazosin, doxycycline, droperidol, econazole, efavirenz, ellipticine, enalapril, enoxacin, enrofloxacin, eperisone, ephedrine, ergotamine, erythromycin, ethambutol, ethionamide, ethopropazine, etoperidone, famotidine, felodipine, fenbendazole, fenfluramine, fenoldopam, fentanyl, fexofenadine, flecainide, flucytosine, flunarizine, flunitrazepam, fluopromazine, fluoxetine, fluphenthixol, fluphenthixol decanoate, fluphenazine, fluphenazine decanoate, flurazepam, flurithromycin, frovatriptan, gabapentin, granisetron, grepafloxacin, guanabenz, halofantrine, haloperidol, hyoscyamine, imipenem, indinavir, irinotecan, isoxazole, isradipine, itraconazole, ketoconazole, ketotifen, labetalol, lamivudine, lansoprazole, leflunomide, levofloxacin, lisinopril, lomefloxacin, loperamide, loratadine, lorazepam, lormetazepam, lysuride, mepacrine, maprotiline, mazindol, mebendazole, meclizine, medazepam, mefloquine, melonicam, meptazinol, mercaptopurine, mesalamine, mesoridazine, metformin, methadone, methaqualone, methylphenidate, methylphenobarbital, methysergide, metoclopramide, metoprolol, metronidazole, mianserin, miconazole, midazolam, miglitol, minoxidil, mitomycins, mitoxantrone, molindone, montelukast, morphine, moxifloxacin, nadolol, nalbuphine, naratriptan, natamycin, nefazodone, nelfinavir, nevirapine, nicardipine, nicotine, nifedipine, nimodipine, nimorazole, nisoldipine, nitrazepam, nitrofurazone, nizatidine, norfloxacin, nortriptyline, nystatin, ofloxacin, olanzapine, omeprazole, ondansetron, omidazole, oxamniquine, oxantel, oxatomide, oxazepam, oxfendazole, oxiconazole, oxprenolol, oxybutynin, oxyphencyclimine, paroxetine, pentazocine, pentoxifylline, perchlorperazine, perfloxacin, perphenazine, phenbenzamine, pheniramine, phenoxybenzamine, phentermine, physostigmine, pimozide, pindolol, pizotifen, pramipexol, pranlukast, praziquantel, prazosin, procarbazine, prochlorperazine, proguanil, propranolol, pseudoephedrine, pyrantel, pyrimethamine, quetiapine, quinidine, quinine, raloxifene, ranitidine, remifentanil, repaglinide, reserpine, ricobendazole, rifabutin, rifampin, rifapentine, rimantadine, risperidone, ritonavir, rizatriptan, ropinirole, rosiglitazone, roxaditine, roxithromycin, salbutamol, saquinavir, selegiline, sertraline, sibutramine, sildenafil, sparfloxacin, spiramycins, stavudine, sulconazole, sulphasalazine, sulpiride, sumatriptan, tacrine, tamoxifen, tamsulosin, temazepam, terazosin, terbinafine, terbutaline, terconazole, terfenadine, tetramisole, thiabendazole, thioguanine, thioridazine, tiagabine, ticlopidine, timolol, tinidazole, tioconazole, tirofiban, tizanidine, tolterodine, topotecan, toremifene, tramadol, trazodone, triamterene, triazolam, trifluoperazine, trimethoprim, trimipramine, tromethamine, tropicamide, trovafloxacin, vancomycin, venlafaxine, vigabatrin, vinblastine, vincristine, vinorelbine, vitamin K5, vitamin K6, vitamin K7, zafirlukast, zolmitriptan, zolpidem, zopiclone, acetazolamide, acetohexamide, acrivastine, alatrofloxacin, albuterol, alclofenac, aloxiprin, alprostadil, amodiaquine, amphotericin, amylobarbital, aspirin, atorvastatin, atovaquone, baclofen, barbital, benazepril, bezafibrate, bromfenac, bumetanide, butobarbital, candesartan, capsaicin, captopril, cefazolin, celecoxib, cephadrine, cephalexin, cerivastatin, cetrizine, chlorambucil, chlorothiazide, chlorpropamide, chlorthalidone, cinoxacin, ciprofloxacin, clinofibrate, cloxacillin, cromoglicate, cromolyn, dantrolene, dichlorophen, diclofenac, dicloxacillin, dicumarol, diflunisal, dimenhydrinate, divalproex, docusate, dronabinol, enoximone, enalapril, enoxacin, enrofloxacin, epalrestat, eposartan, essential fatty acids, estramustine, ethacrynic acid, ethotoin, etodolac, etoposide, fenbufen, fenoprofen, fexofenadine, fluconazole, flurbiprofen, fluvastatin, fosinopril, fosphenytoin, fumagillin, furosemide, gabapentin, gemfibrozil, gliclazide, glipizide, glybenclamide, glyburide, glimepiride, grepafloxacin, ibufenac, ibuprofen, imipenem, indomethacin, irbesartan, isotretinoin, ketoprofen, ketorolac, lamotrigine, levofloxacin, levothyroxine, lisinopril, lomefloxacin, losartan, lovastatin, meclofenamic acid, mefenamic acid, mesalamine, methotrexate, metolazone, montelukast, nalidixic acid, naproxen, natamycin, nimesulide, nitrofurantoin, non-essential fatty acids, norfloxacin, nystatin, ofloxacin, oxacillin, oxaprozin, oxyphenbutazone, penicillins, pentobarbital, perfloxacin, phenobarbital, phenytoin, pioglitazone, piroxicam, pramipexol, pranlukast, pravastatin, probenecid, probucol, propofol, propylthiouracil, quinapril, rabeprazole, repaglinide, rifampin, rifapentine, sparfloxacin, sulfabenzamide, sulfacetamide, sulfadiazine, sulfadoxine, sulfamerazine, sulfamethoxazole, sulfafurazole, sulfapyridine, sulfasalazine, sulindac, sulphasalazine, sulthiame, telmisartan, teniposide, terbutaline, tetrahydrocannabinol, tirofiban, tolazamide, tolbutamide, tolcapone, tolmetin, tretinoin, troglitazone, trovafloxacin, undecenoic acid, ursodeoxycholic acid, valproic acid, valsartan, vancomycin, verteporfin, vigabatrin, vitamin K-S (II), zafirlukast, and pharmaceutically acceptable oil-soluble derivative and salts thereof.

Anti-infective Agents

Anti-infective agents include antibacterial, antifungal, antiviral, and anti-parasitic agents.

Antibacterial Agents

One important class of active agents comprises antibacterial agents. It is well known that bacterial infections are involved in a variety of superficial and non-superficial disorders of the skin and mucosal membranes. The antibacterial agent can be active against gram positive and gram-negative bacteria, protozoa, aerobic bacteria and anaerobes. The composition of the invention may include one or a combination of water soluble, oil soluble and suspended antibacterial agents.

Specific oil-soluble species of macrolide antibiotics, such as erythromycin; sulfonamide (in its base form), such as sulfanilamide, sulfadiazine and sulfacetamide; mupirocin; tetracyclines, such as tetracycline and doxycycline; specific oil-soluble species of synthetic and semi-synthesic penicillins and beta-lactams; cloramphenicol; specific oil-soluble species of imidazoles; dicarboxylic acids, such as azelaic acid; salicylates; peptide antibiotics; cyclic peptides, such as cyclosporine, tacrolimus, pimecrolimus and sirolimus (rapamycin); and non-specific antibacterial agents such as strong oxidants and free radical liberating compounds, bleaching agents, iodine compounds and benzoyl peroxide.

Antibacterial compositions according to the present invention may be used to treat infections of the skin. An example of a very common skin infection is impetigo, a bacterial disease caused by *Staphylococcus aureus* and *beta-hemolytic streptococci*, which mainly afflicts children and infants. Various antibacterial creams and ointments, such as mupirocin cream and mupirocin ointment, have been utilized to treat impetigo, however, treatment compliance is markedly impaired due to the fact that children resist the extensive rubbing involved in cream and ointment treatment. Foam, on the other hand, was found to be easily applied, without any difficulty. It has been surprisingly discovered that a composition of mupirocin n a vehicle containing PEG (as a potent solvent), a non-ionic surfactant and a gelling agent, where the non-ionic surface-active agent at a concentration of 2% by weight and the total amounts of surface-active agent is in the range of 2.5% by weight, and propellan, afforded an excellent foam which was stable upon discharge fromt eh aerosol can and was easy to apply onto an afflicted area.

The composition of the present invention is particularly useful and beneficial in the prevention and treatment of secondary infections, accompanying skin-structure damage, such as in cuts, wounds, burns and ulcers. In all such cases, the present formulation is easy to use, being in foam state upon application and absorbing into the skin instantly upon gentle application.

While being useful in the prevention and treatment of infections, the antibacterial foam of the present invention is also applicable for decontaminating areas, afflicted with bacterial warfare organisms, such as anthrax and smallpox.

Anti-fungal Agents

Fungal infections are another object of treatment using the composition of the present invention. Superficial fungal infection of the skin is one of the most common skin diseases seen in general practice. Dermatophytosis is probably the most common superficial fungal infection of the skin. It is caused by a group of fungi, which are capable of metabolizing the keratin of human epidermis, nails or hair. There are three genera of dermatophytes causing dermatophytosis, i.e, microsporum, trichophyton and epidermophyton.

Candidiasis is an infection caused by the yeast like fungus *candida albicans* or occasionally other species of *candida*. Clinical syndromes of candidiasis include: (a) oral candidiasis (thrush); (b) candidiasis of the skin and genital mucous membrane; and (c) candida paronychia, which inflicts the nail and nail bed.

The foam composition of the present invention may comprise an antifungal drug, which is active against *dermatophytes* and *candida*, selected from the group of, but not limited to azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and any combination thereof at a therapeutically effective concentration.

The composition of the present invention is useful for example for the treatment and prevention of *tinea corporis, tinea pedis, tinea rubrum, tinea unguium, tinea cruris, tinea barbae* and *tinea versicolor*, as well as yeast infections, such as candidiasis, and candidal vaginitis.

Anti-viral Agents

The composition of the present invention is particularly beneficial in treating and preventing viral infections. Cold sores are caused by the herpes simplex Type 1 virus and are sometimes referred to as facial herpes. Mollusca are small viral growths that appear singly or in groups on the face, trunk, lower abdomen, pelvis, inner thighs, or penis. Shingles (herpes zoster), which usually only occurs once in a lifetime, appears as a rash (clusters of blisters with a red base). It is caused by the same virus responsible for chickenpox. Warts are a common, benign skin tumor caused by viral infection.

Any known antiviral agent, in a therapeutically effective concentration, can be incorporated in the foam composition of the present invention. The composition of the present invention, which comprises a hydrophobic solvent, would facilitate an enhanced rate of penetration and better topical distribution of any of the above listed antiviral drugs.

Anti-inflammatorv or Anti-allergic Agents

Yet, according to another embodiment according to the present invention the active agent is an anti-inflammatory or anti-allergic agent. Anti-inflammatory agents can be selected from the group of corticosteroids, non-steroidal anti-inflammatory drugs (NSAIDs), anti-histamines, immunosuppressant agents, immunomodulators; and any combination thereof at a therapeutically effective concentration.

The following table provides a summary of currently available corticosteroid agent and their typical therapeutically effective concentration.

| Potency | Compound | Current products |
| --- | --- | --- |
| Very high | Clobetasol proprionate | Cream or ointment 0.05% |
| | Halobetasol proprionate | Cream or ointment 0.05% |
| High | Betamethasone diproprionate | Cream or ointment 0.05% |
| | Betamethasone valerate | Ointment 0.1% |
| | Fluocinolone acetonide | Cream 0.02% |
| | Halcinonide | Cream or ointment 0.1% |
| Medium | Betamethasone valerate | Cream 0.1% |
| | Fluocinolone acetonide | Cream or ointment 0.020% |
| | Hydrocortisone valerate | Cream or ointment 0.2% |
| | Triamcinolone acetonide | Cream, ointment, or lotion 0.1% or 0.020% |
| Low | Hydrocortisone | Cream, ointment, or lotion 1.0% or 2.5% |

The concentrations of corticosteroid drugs, as presented in the above table are provided herein only as example, and any therapeutically effective concentration of such corticosteroids can be incorporated in the composition of the present invention.

Since corticosteroid drugs are typically hydrophobic, the composition of the present invention, comprising a hydrophobic solvent, is most suitable as a vehicle to facilitate better topical distribution, improved occlusion and an enhanced rate of penetration of any of the above listed drugs.

Corticosteroids are used for treating psoriasis. Psoriasis is a very common chronic skin disease, which may be the target of treatment using the composition of the present invention. It is marked by periodic flare-ups of sharply defined red patches covered by a silvery, flaky surface.

Corticosteroid ointments, greasy preparations containing little or no water, are typically used for treating psoriasis. Their main disadvantage is in their sticky feeling, which remains so long after treatment is over. By contrast, the foam of the present invention, while comprising considerable concentration of an oil (hydrophobic solvent), spreads very easily throughout the afflicted area and absorbs into the skin without leaving any untoward sensation or look.

Other non-limiting examples of inflammatory disorders, which can be prevented or treated by the oleaginous compositions of the present invention, wherein the drug is a steroid are atopic dermatitis, seborrhea, seborrheic dermatitis of the face and trunk, seborrheic blepharitis, contact dermatitis, stasis dermatitis (gravitational eczema; varicose eczema), exfoliative dermatitis (erythroderma), lichen simplex chronicus, pityriasis rosea and pemphigus.

It is pointed out that certain of the solvents that may be used in the preparation of the composition of the present invention including polyunsaturated fatty acids, containing omega-3 and omega-6 fatty acids (e.g., linoleic and linolenic acid, gamma-linoleic acid (GLA), eicosapentaenoic acid (EPA) and docosahexaenoic acid (DHA) are themselves beneficial in the treatment of psoriasis and other skin inflammation conditions.

A second class of anti-inflammatory agents, which is useful in the foam of the present invention, includes the nonsteroidal anti-inflammatory agents (NSAIDs). The variety of compounds encompassed by this group is well-known to those skilled in the art. Specific non-steroidal anti-inflammatory agents useful in the composition invention include, but are not limited to:

Oxicams, such as piroxicam, isoxicam, tenoxicam, sudoxicam;

Salicylates, such as salicylic acid, ethyl salicylate, methyl salyicilate, aspirin, disalcid, benorylate, trilisate, safapryn, solprin, diflunisal, and fendosal;

Acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

Fenamates, such as mefenamic, meclofenamic, flufenamic, niflumic, and tolfenamic acids;

Propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and Pyrazoles, such as phenylbutazone, oxyphenbutazone, feprazone, azapropazone, and trimethazone.

Any further steroidal and nonsteroidal compounds, having the capacity to prevent, alleviate the symptoms of, treat or cure inflammation processes, are generally included, as possible anti-inflammatory agents, according to the present invention.

Topical antihistaminic preparations currently available include 1% and 2% diphenhydramine, 5% doxepin, phrilamine maleate, chlorpheniramine and tripelennamine, phenothiazines, promethazine hydrochloride and dimethindene maleate. These active agents, as well as additional antihistamines can also be incorporated in the composition of the present invention.

The therapeutic composition of the present invention may also comprise an anti-inflammatory or antiallergic agent, wherein said agent reduces the occurrence of pro-inflammatory cytokines or inhibits the effect of pro-inflammatory cytokines. Mixtures of such anti-inflammatory agents may also be employed, as well as the dermatologically acceptable salts, esters, amides, prodrugs and derivatives of these agents.

Topical application of a foam, comprising a safe and effective dose of an NSAID can be useful in the prevention and/or alleviation of the symptoms of rheumatoid arthritis, osteoarthritis and pain. Topical NSAIDs, incorporated in the foam of the present invention can be also used in the treatment of dermatological disorders, such as acne, rosacea, hair growth disorders, actinic keratosis and certain skin cancer conditions.

Immunosuppressant agents, immunoregulating agents and immunomodulators are chemically or biologically-derived agents that modify the immune response or the functioning of Pyrazoles, such as phenylbutazone, oxyphenbutazone, feprazone, azapropazone, and trimethazone.

Any further steroidal and nonsteroidal compounds, having the capacity to prevent, alleviate the symptoms of, treat or cure inflammation processes, are generally included, as possible anti-inflammatory agents, according to the present invention.

Topical antihistaminic preparations currently available include 1% and 2% diphenhydramine, 5% doxepin, phrilamine maleate, chlorpheniramine and tripelennamine, phenothiazines, promethazine hydrochloride and dimethindene maleate. These active agents, as well as additional antihistamines can also be incorporated in the composition of the present invention.

The therapeutic composition of the present invention may also comprise an anti-inflammatory or antiallergic agent, wherein said agent reduces the occurrence of pro-inflammatory cytokines or inhibits the effect of pro-inflammatory cytokines. Mixtures of such anti-inflammatory agents may also be employed, as well as the dermatologically acceptable salts, esters, amides, prodrugs and derivatives of these agents.

Topical application of a foam, comprising a safe and effective dose of an NSAID can be useful in the prevention and/or alleviation of the symptoms of rheumatoid arthritis, osteoarthritis and pain. Topical NSAIDs, incorporated in the foam of the present invention can be also used in the treatment of dermatological disorders, such as acne, rosacea, hair growth disorders, actinic keratosis and certain skin cancer conditions.

Immunosuppressant agents, immunoregulating agents and immunomodulators are chemically or biologically-derived agents that modify the immune response or the functioning of the immune system (as by the stimulation of antibody formation or the inhibition of white blood cell activity). Immunosuppressant agents and immunomodulators include, among other options, cyclic peptides, such as cyclosporine, tacrolimus, tresperimus, pimecrolimus, sirolimus (rapamycin), verolimus, laflunimus, laquinimod and imiquimod. Such compounds, delivered in the foam of the present invention, are especially advantageous in skin disorders such as psoriasis, eczema and atopic dermatitis, where the large skin areas are to be treated. The oleaginous foam compositions of the present invention provide excellent vehicles for such applications and are superior to conventional creams and ointments.

Topical Anesthetics

The compositions of the present invention may comprise a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof. Mixtures of such anesthetic agents may be synergistically beneficial.

Keratolytically Active Agents

The term "keratolytically active agent" refers herein to a compound which loosens and removes the stratum corneum of the skin, or alters the structure of the keratin layers of skin.

Keratolytically active agents are used in the treatment of many dermatological disorders, which involve dry skin, hyperkeratinization (such as psoriasis), skin itching (such as xerosis), acne and rosacea.

Suitable keratolytically active agents include phenol and substituted phenolic compounds. Such compounds are known to dissolve and loosen the intracellular matrix of the hyperkeratinized tissue. As such, they are used in the treatment of dermatological disorders. Dihydroxy benzene and derivatives thereof have been recognized as potent keratolytic agents. Resorcinol (m-dihydroxybenzene) and derivatives thereof are used in anti-acne preparations. Hydroquinone (p-dihydroxybenzene), besides its anti-pigmentation properties, is also keratolytic. These compounds also exhibit antiseptic properties. Cresols also possess bactericidal and keratolytic properties.

Vitamin A and its derivatives, such as retinoic acid, isoretinoic acid, retinol and retinal are another preferred class of keratolytically active agents.

Another group of keratolytically active agents include alpha-hydroxy acids, such as lactic acid and glycolic acid and their respective salts and derivatives; and beta-hydroxy acids, such as Salicylic acid (o-hydroxybenzoic acid) and its salts and pharmaceutically acceptable derivatives, which typically possess anti-inflammatory, as well as keratolytic, activity.

Yet, another class of preferred keratolytically active agents includes urea and its derivatives.

Retinoids

Another preferred group of active agents includes, for example, retinol, retinal, all trans retinoic acid and derivatives, isomers and analogs thereof, collectively termed "retinoids". Etretinate, actiretin, isotretinoin, adapalene and tazarotene are further examples of said retinoid isomers and analogs. Compositions according to the present invention, which comprise retinoids as the active agent, can be used for the treatment of acne, seborrhea, various dermatoses, inflammation of the skin, mucosal membranes, vagina and the rectum, psoriasis, actinic keratosis and skin cancers, by application onto the affected area.

Insecticide and Insect Rrepellents Agents

Insects, such as mosquitoes, biting flies, mites, gnats, fleas, chiggers, punkies, sand flies, lice and ticks can be annoying and sometimes pose a serious risk to human and animal health. In certain areas of the United States, mosquitoes can transmit diseases like equine and St. Louis encephalitis. Biting flies can inflict a painful bite that can persist for days, swell, and become infected. Ticks can transmit serious diseases like Lyme disease and Rocky Mountain spotted fever.

There are several types of insect repellents to use when protecting people and animals from flying or biting insects, spiders, ticks and mites. By way of example, these may include DEET (N, N-diethyl-m-toluamide), dimethyl phthalate, piperonyl butoxide and permethrin. Insect repelling terpenoids, have been reported by Hwang, et al, J. Chem. Ecol., 11, 1297 (1985); and Ruledge, J. Am. Mosquito Control Assoc. 4, 414 (1988).

A particularly preferred group of insect repellents includes the terpenoid compounds, described in U.S. Pat. No. 5,411, 992, including:

Terpenoid-alcohol or terpene-ols are terpenoids which have at least one hydroxyl group. Examples of terpene-ols include: C10H16O compounds, perillyl alcohol, carveol, myrtenol, and cis-verbenol; C10H18O compounds, myrtanol, iso-pinocampheol, dihydrocarveol, isopulegol, terpineol, terpinen-4-ol, nerol, geraniol, and linalool, and C10H20O compounds, menthol, beta-citronellol, and dihydro-myrcenol.

Terpenoid-esters are terpenoids, which have at least one ester group which is the product of the bonding of the hydroxyl group of a terpene-ol with an aliphatic carboxylic acid that can contain functional groups such as the hydroxyl or amine on the aliphatic chain. Examples of suitable aliphatic carboxylic acids include acetic acid, propionic acid, lactic acid, and various amino acids. Examples of terpenoid-esters include: carvyl acetate, carvyl propionate, and menthyl lactate.

Essential oils which contain terpenoids and perfumes which contain terpenoids. Non-limiting examples of essential oils which have high content of terpene-ols and esters include bergamot (62% terpenoids); sage (>50% terpenoids); styrax (>50% terpenoids); peppermint (>50% terpenoids); and pine Siberian (75% terpenoids %). Terpenes, aldehydes and ketones vary in their usefulness but as a general group have potential as insect-repellent.

The oleaginous foams of the present invention are particularly suitable for the effective uniform spreading of an insect repellent agent onto large areas of the skin of humans and animals. The hydrophobic solvent present in the foam composition helps retain the insect repellent on the skin surface for an extended period of time.

Yet, in a further embodiment, the foams of the present invention are suitable for delivery of insect-killing agents (insecticides) to an afflicted external surface area of humans and animals. Thus, the pharmaceutical or cosmetic composition of the present invention may comprise an insecticide, known in the art of parasitology. By way of example, such insecticide can be selected selected from the group of permethrin, hexachlorobenzene, carbamate, naturally occuring pyrethroids, permethrin, allethrin, malathion, piperonyl butoxide and any combination thereof at a therapeutically effective concentration. Its application is very convenient and it spreads easily, even over hairy areas. The hydrophobic solvent present in the foam composition helps retain the insecticide on the treated area for an extended period of time. Furthermore, the presence of a hydrophobic solvent in the foam of the present invention eases mechanical removal of lice and nits with a comb.

Anti Cancer Agents

Anti cancer agents can also be used according to the present invention as the drug of choice from skin malignant tumors, such as basal cell carcinoma, squamous sell carcinoma, melanoma and Kaposi's sarcoma, as well as the precancerous condition actinic keratosis. In certain cases, topical cytotoxic and antiproliferative drugs are used to treat or prevent such cancers, including 5-fluorouracil, also called 5-FU. 5-FU, as well as any other anti-cancer agents, know in the art of cancer medicine, can be incorporated in the foam at therapeutically effective levels.

A preferred family of anticancer drugs, suitable for usage in the foam of the present formulation comprises anti-estrogens, such as tamoxifen.

Photodynamic Therapy Agents

The foam compositions of the present invention are also useful to deliver photo-sensitizing agents, known in the art of photodynamic therapy. By way of example, such photosensitizers can be selected from the group comprising modified porphyrins, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives, as well as photosensitizer precursors, such as aminolevulinic acid (ALA).

Active Agents for Burns, Wounds, Cuts and Ulcers

The treatment of burns, wounds, cuts and ulcers, using the composition of the present invention is particularly advantageous. The oleaginous foam compositions of the present invention may comprise a combination of anti-infective agents (against bacteria, fungi and/or viruses), anti-inflammatory agents (steroidal and/or NSAIDs) and pain relieving components. Upon application, the foam spreads easily, covering the surface of the affected area, and without causing pain.

Cosmetic Active Agents

The oleaginous foams of the present invention are useful and advantageous for skin care and cosmetic care. The combination of oil, having refatting, protective and moisture-retaining properties, in a spreadable foam form, can be used to substitute currently used cosmetic skin care creams, lotions, gels, etc. The foam compositions of the present invention, with or without further active ingredients, are suitable for the further application as "cosmeceutical" preparation (cosmetic products with therapeutic benefit), to treat "cosmetic" skin disorders, such as aging skin, wrinkles, hyperpigmentation (melasma, chloasma, freckles, etc.), scaly skin and other skin undesirable properties.

The CTFA Cosmetic Ingredient Handbook describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, astringents, etc. (e.g., clove oil, menthol, camphor, eucalyptus oil, eugenol, menthyl lactate, witch hazel distillate), anti-acne agents, anti-caking agents, antifoaming agents, anti-microbial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, and vitamins and derivatives thereof.

In one embodiment the active agent is a cosmetic agent selected from a retinoid, an anti-wrinkle agent, a radical scavenger, a self-tanning agent, a skin whitening agent, a skin protective agent, an anti-cellulite agent, a massaging oil and an anti-wart agent.

Anti-acne and Anti-wrinkle Active Agents

The compositions of the present invention may comprise a safe and effective amount of one or more pharmaceutically or cosmetically acceptable anti-acne active agents. Examples of useful anti-acne actives include resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, zinc salts and complexes, and combinations thereof, in a therapeutically effective concentration. Certain anti-acne agents from this list are also useful in the treatment of other skin disease, such as psoriasis, eczema and atopic dermatitis.

Anti-wrinkle Active Agents/anti-atrophy Active Agents and Agents to Treat Dry and Scaly Skin (Xerosis and Ichthyosis).

The compositions of the present invention may further comprise a safe and effective amount of one or more anti-wrinkle actives or anti-atrophy actives, which can be easily delivered by spreading a foam onto the skin. Exemplary anti-wrinkle/anti-atrophy active agents suitable for use in the compositions of the present invention include sulfur-containing D and L amino acids and their derivatives and salts, particularly the N-acetyl derivatives; thiols; hydroxy acids (e.g., alpha-hydroxy acids such as lactic acid and glycolic acid and their derivatives and salts; or beta-hydroxy acids such as salicylic acid and salicylic acid salts and derivatives), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate). In the case of dry, scaly skin (xerosis) and ichthyosis such agents can alleviate the symptoms by temporary relief of itching associated with these conditions.

Anti-oxidants/Radical Scavengers

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox.sup.R), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

The foam of the present invention is suitable for delivering skin protecting and revitalizing anti-oxidants/radical scavengers. It is further pointed out that polyunsaturated fatty acids, containing omega-3 and omega-6 fatty acids (e.g., linoleic and linolenic acid, gamma-linoleic acid (GLA), eicosapentaenoic acid (EPA) and docosahexaenoic acid (DHA) are beneficial in the treatment of psoriasis and other skin inflammation conditions. Likewise, emollients and silicone oils exert moisture-retaining and skin protective effects on the skin. Thus in a preferred embodiment, a skin protective foam is provided, wherein the hydrophobic solvent comprises in full or in part, a solvent, selected from the group of emollients, silicone oil and oils, rich in unsaturated fatty acids, thus, affording a synergistic therapeutic effect of the anti-oxidants/radical scavenger agent and the vehicle components.

Self-tanning Active Agents

The oleaginous foams of the present invention are particularly suitable for the uniform delivery of a tanning active agent onto large areas of the skin. It is preferable that the compositions comprise from about 0.1% to about 20%, more preferably from about 2% to about 7%, and still more preferably from about 3% to about 6% of the composition, of dihydroxyacetone, or any other compound, know in the art as an artificial tanning active agent.

Solid Matter Agents

According to a preferred embodiment of the present invention, the at least one active agent comprises solid matter or particulate matter i.e., material that is not soluble in the liquid carrier composition of the foamable composition. For definition purposes, solid matter shall mean material that is not soluble in the foamable composition more than 10% of the concentration intended to be included in said foamable composition. The concentration of the solid matter in the foamable composition is from about 1% to about 20% w/w. In one or more embodiments, the concentration of solid matter in the composition is from about 2% to about 16% w/w.

By way of example, the following classes of solid matter substances are presented.

Metallic oxides, such as titanium dioxide, zinc oxide, zirconium oxide, iron oxide. Preferably, as used in the present invention, titanium dioxide has an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. In one embodiment the metal oxides are present in the amount of from about 0.1% to about 20%, preferably from about 0.5% to about 16%, more preferably from about 1% to about 10%, of the composition. In yet another embodiment, such solids are micronized to form particles having primary size of less than 15 nm.

Silicon containing solid matter includes silicone oxide, also termed "silica", "fumed silica" and "silica gel", a white or colorless insoluble solid (SiO2); and talc, which is fine grained mineral consisting of hydrated magnesium silicate;

Carbon, for example in the form of amorphous carbon or graphite;

Oxidizing agents, such as benzoyl peroxide, calcium and magnesium hypochlorite;

Metallic Silver, in small particles, including nanocrystalline silver, which is used for antibacterial and wound healing purposes; other metal particles and mineral particles Cosmetic scrub materials, including, for example meals of strawberry seeds, raspberry seeds, apricot seeds, sweet almond, cranberry seeds;

Pigments, which are insoluble in the foamable composition.

When such solid matter agents are included in the oleaginous foamable composition of the present invention, a novel foam product, combining the refatting, occlusive and protective properties of the oleaginous foam carrier and the beneficial properties of the solid matter agent is afforded. Thus, several unique products can be provided, as exemplified herein:

Generally, products for the prevention and treatment of diaper dermatitis and for skin protection are provided in the form of paste that is intended for application on the baby's posterior, under the diaper. The paste typically includes about 30% oil and/or petrolatum, and about 10% zinc oxide, which are intended to provide a protective barrier between the baby's skin and the irritating environment inside the diaper. While containing the right ingredients, current baby pastes are very viscous and thick, and therefore hard to spread on the target area.

The oleaginous foam for treating or preventing diaper rash of the present invention comprises the following ingredients:

at least one solvent selected from a hydrophobic solvent, a co-solvent, an emollient and mixtures thereof, at a concentration of about 30% to about 90%, preferably between about 30% to about 70% water at a concentration of 1% to about 60%;

about 6% to about 20% zinc oxide (or an alternative metal oxide)

at least one non-ionic lipophilic surface active agent, preferably having an HLB value of about 3 to about 10, more preferably about 3.5 to about 9 at a concentration of about 0.1% to about 10%, or between about 0.1% and about 5%;

at least one gelling agent at a concentration of about 0.1% to about 5%;

a liquefied or compressed gas propellant at a concentration of about 3% to about 25% of the total composition, in an aerosol container.

Such foam is superior to current pastes in that it is very fluffy and light. Upon discharge from the aerosol can, it creates a mass, having density between 0.04 gr/mL and 0.2 gr/mL, which is very easy to spread evenly and uniformly on the target area. There is no need to rub thoroughly and therefore, application of the foam does not cause any discomfort to the baby, unlike conventional baby pastes. Following application and spreading of the foam, a protective layer is formed, which is water resistant, and does not wash out under a stream of tap water.

Foam for diaper dermatitis and/or skin protection can further comprise anti-irritant and/or infective agents, such as corticosteroids, anti-inflammatory, anti-allergic, anti-fungal and anti-microbial agents.

Skin-Lightening and Whitening Agents

The foam of the present invention is particularly suitable for the uniform delivery of a skin-lightening agent. When used, the compositions preferably comprise from about 0.1% to about 10%, more preferably from about 0.2% to about 5%, of the composition, of a skin-lightening agent. Suitable skin lightening or whitening agents include those known in the art, including hydroquinone, azelaic acid and other related dicarboxylic acids, and salts and derivatives thereof, retinoids, kojic acid, arbutin, nicotinic acid and its precursors, salts and derivatives, ascorbic acid and salts and derivatives thereof (e.g., magnesium ascorbyl phosphate or sodium ascorbyl phosphate), and herbal extracts (e.g., mulberry extract, placental extract).

In one or more embodiments of the present invention, the foam composition comprises a combination of a skin-whitening agent and a sunscreen agent.

In one or more embodiments of the present invention, the foam composition comprises a combination of a skin-whitening agent and an inorganic sunscreen agent. When inorganic sunscreen agents, e.g. Ti02, are rubbed onto the skin, they leave a white coating, which provides an immediate (although transient) whitening effect, which is highly desirable by the consumer, who wishes to see instant change in his/her appearance. The whitening agent, in combination with the inorganic sunscreen agent in the foam carrier can be easily and uniformly distributed on the skin surface, thereby affording an even instant whitening effect, unlike creams that are difficult to spread evenly on skin areas.

Use of a Solvent, Surface Active Agent, Foam Adjuvant and Polymeric Agent as an Active Agent.

According to one embodiment, the at least one active agent is selected from the group of solvent, surface active agent, foam adjuvant and gelling agent, which are, on a case by case basis known to possess a therapeutic benefit.

Composition and Foam Physical Characteristics

Composition Flow Properties

It is desirable to have an oleaginous foam composition, including solvents, formulation excipients, water (as applicable), active agents and propellant, in a stable formulation, which provides acceptable shelf-life of the product.

Yet, another crucial property of a composition is its level of flow, since a composition that is not free flowing cannot flow through the dip-tube of the aerosol container and create acceptable foam. It has been noted that in the context of the composition of the present invention, compositions comprising semi-solid hydrophobic solvents, e.g., white petrolatum, are excessively viscous and demonstrate poor flowability.

The combination of at least one surface active agent, at least one foaming adjuvant and at least one gelling agent, according to one or more embodiments of the invention provides a low specific gravity foam having superior expandability, flow properties and sheer breakability (among other attributes). According to one or more embodiments of the present invention, the total amount of at least one surface active agent, at least one foam adjuvant (optional) and at least gelling agent, in combination does not exceed 8% (w/w) of foamable composition. In other embodiments, the combined amounts of at least one surface active agent, at least one foaming adjuvant and at least one gelling agent is less than 5% (w/w) of foam composition. The low solid content improves the flow properties of the foam, reduces unpleasant skin residue and reduces the cost of manufacture. As is demonstrated herein, the foam stability and expandability are excellent, despite the low levels of these components in the foam.

Expandability

Expandability is an important feature of a product, intended to treat large surface areas and internal cavities of the body. Thus, in one embodiment of the present invention, the specific gravity of the foam, upon discharge from the aerosol can is between about 0.02 gr/mL and 0.5 gr/mL, more preferably between about 0.04 gr/mL and about 0.2 gr/mL Foam Physical Characteristics In terms of foam consistency and texture an acceptable foam is one, that exhibits the following characteristics:

Upon release from the aerosol can, creates a foam mass, which is sustained on a surface for at least one minute;

Foam texture should vary from a very fine creamy foam to a fine bubble structure;

Foam has to have specific gravity in the range of about 0.02 gr/mL to about 0.5 gr/mL, more preferably between about 0.04 gr/mL and about 0.2 gr/mL.

In terms of spreadability and absorption an acceptable foam is one, that:

Does not readily collapse upon dispensing on the skin;

Spreads easily on a skin surface;

Substantially absorbed following rubbing onto the skin.

In terms of organoleptic properties an acceptable foam is one, that:

Creates a pleasant feeling after application;

Leaves minimal oily residue;

Leaves minimal shiny residual look.

The following scale for foam quality is used to evaluate foams.

E (excellent): very rich and creamy in appearance, does not show any bubble structure or shows a very fine (small) bubble structure.

G (good): rich and creamy in appearance, very small bubble size, "dulls" more rapidly than an excellent foam.

FG (fairly good): a moderate amount of creaminess noticeable, bubble structure is noticeable.

F (fair): very little creaminess noticeable, larger bubble structure than a "fairly good" foam.

P (poor): no creaminess noticeable, large bubble structure.

VP (very poor): dry foam, large very dull bubbles, difficult to spread on the skin.

Foam Stability and Breakability

In one or more embodiments, the foam compositions are desirably stable for a long period of time. Thus, the foam composition does not undergo phase separation following at least two freeze/thaw cycles.

According to further embodiments, upon discharge from an aerosol can onto a mucosal membrane at about 37° C., the foam expands to reach its designated volume and stays stable as a foam for at least 60 seconds following application, or about 2 minutes, or even about 3 minutes.

A crucial aspect of foam properties, according to the present invention is breakability. Sheer-force breakability of the foam, as attained by the composition of the present invention is clearly advantageous to thermally-induced breakability, present, for example in U.S. Pat. No. 6,126,920, and the respective Olux® and Luxiq® products, as demonstrated by the fact that according to the use instructions of Olux® and Luxiq®, the foam cannot be applied on the hand and afterwards delivered to the afflicted area, since it collapses upon exposure to skin temperature.

Further Technical Parameters

The composition of the present invention may be contained in and dispensed from a container capable of withstanding the pressure of the propellant gas and having an appropriate valve/nozzle for dispensing the composition as foam under pressure. A customary liquefied or compressed gas propellant can be added, in the amount of about 3 to about 25% of the total composition. Liquefied propellants are gases that exist as liquids under pressure, including high purity hydrocarbons such as propane, isobutane and n-butane, dimethyl ether and chlorofluorocarbons (CFCs). Compressed gasses are exemplified by air, nitrogen and carbon dioxide.

A specific embodiment according to the present invention comprises placing the composition of the present invention on a patch, occlusive tape or the skin-contact compartment of a transdermal delivery apparatus and applying such object onto the skin, in order to attain effective superficial treatment or enhanced penetration of the drug into the skin or through the skin.

Utilizing such strategy, one can apply drugs, which are currently administered systemically or that require transdermal delivery, in the preferred therapeutic system of the present invention. Examples for such drugs are nicotine, testosterone and other male hormones and male hormone precursors, estrogen and other female hormones and hormone precursors, growth hormone, insulin, caffeine, steroidal and non-steroidal antiinflammatory agents and thyroid hormone substitutes.

The therapeutic composition according to the present invention can also be used to prepare cosmetics for beauty purpose by adding into skin care agents and perfume.

Metered Dosing

In order to provide proper therapy, precise dosing is advantageous. According to one preferred embodiment, the foam therapeutic product is adapted for storage in an aerosol container having a metered dose valve associated therewith for dispensing an accurate dose of drug in the form of a foam. More preferably, the metered dose valve is selected to release a foam in a volume that will allow effective spreading of the active agent throughout the body surface with substantially minimal overdose.

In one or more embodiments, the meter dose valve provides a unit dose of between about 10 μL and about 1000 μL. Assuming a representative foam density (specific gravity) of 0.06 g/mL, a 10 μL valve provides a volume of about 0.17 mL of foam, and a 1000 μL metered dose valve provides about 17 mL of foam. Thus, by selecting a specific metered dosing valve and adjusting the foam density by fine tuning formulation parameters and adjusting the ration between the liquid components of the composition and the propellant, one can design an adequate dosage form according to the specific target body surface.

Fields of Pharmaceutical Applications

By including an appropriate therapeutic agent in the foamable carrier, the foam composition of the present invention is useful in treating a patient having a any one of a variety of dermatological disorders (also termed "dermatoses"), such as classified, in a non-limiting exemplary manner, according to the following groups:

Dermatitis including Contact Dermatitis, Atopic Dermatitis, Seborrheic Dermatitis, Nummular Dermatitis, Chronic Dermatitis of the hands and feet, Generalized Exfoliative Dermatitis, Stasis Dermatitis; Lichen Simplex Chronicus; Diaper rash; Bacterial Infections including Cellulitis, Acute Lymphangitis, Lymphadenitis, Erysipelas, Cutaneous Abscesses, Necrotizing Subcutaneous Infections, Staphylococcal Scalded Skin Syndrome, Folliculitis, Furuncles, Hidradenitis Suppurativa, Carbuncles, Paronychial Infections, Erythrasma; Fungal Infections including Dermatophyte Infections, Yeast Infections; Parasitic Infections including Scabies, Pediculosis, Creeping Eruption; Viral Infections; Disorders of Hair Follicles and Sebaceous Glands including Acne, Rosacea, Perioral Dermatitis, Hypertrichosis (Hirsutism), Alopecia, including male pattern baldness, alopecia areata, alopecia universalis and alopecia totalis; Pseudofolliculitis Barbae, Keratinous Cyst; Scaling Papular Diseases including Psoriasis, Pityriasis Rosea, Lichen Planus, Pityriasis Rubra Pilaris; Benign Tumors including Moles, Dysplastic Nevi, Skin Tags, Lipomas, Angiomas, Pyogenic Granuloma, Seborrheic Keratoses, Dermatofibroma, Keratoacanthoma, Keloid; Malignant Tumors including Basal Cell Carcinoma, Squamous Cell Carcinoma, Malignant Melanoma, Paget's Disease of the Nipples, Kaposi's Sarcoma; Reactions to Sunlight including Sunburn, Chronic Effects of Sunlight, Photosensitivity; Bullous Diseases including Pemphigus, Bullous Pemphigoid, Dermatitis Herpetiformis, Linear Immunoglobulin A Disease; Pigmentation Disorders including Hypopigmentation such as Vitiligo, Albinism and Postinflammatory hypopigmentation and Hyperpigmentation such as Melasma (chloasma), Drug-induced hyperpigmentation, Postinflammatory hyperpigmentation; Disorders of Cornification including Ichthyosis, Keratosis Pilaris, Calluses and Corns, Actinic keratosis; Pressure Sores; Disorders of Sweating; Inflammatory reactions including Drug Eruptions, Toxic Epidermal Necrolysis; Erythema Multiforme, Erythema Nodosum, Granuloma Annulare.

The oleaginous compositions of the present invention are useful in the therapy of non-dermatological disorders, which respond to topical/transdermal delivery of an active agent. By way of example, such disorders include localized pain in general, as well as joint pain, muscle pain, back pain, rheumatic pain, arthritis, ostheoarthritis and acute soft tissue injuries and sports injuries. Other disorders of this class include conditions, which respond to hormone therapy, such as hormone replacement therapy, transdermal nicotine administration, and other respective disorders, known in the art of drug delivery.

The oleaginous compositions of the present invention are further useful for the treatment and prevention of disorders and diseases of other body cavities including the rectum, vagina, penile urethra and ear canal.

Thus, the oleaginous foam compositions of the present invention are useful in treating a patient having any one of a variety of gynecological disorders, such as classified, in a non-limiting exemplary manner, according to the following groups:

Pelvic pain, including premenstrual syndrome (PMS), mittelschmerz (severe midcycle pain due to ovulation), dysmenorrhea (pain related to the menstrual cycle), endometriosis, ectopic pregnancy, ovarian cysts and masses, acute pelvic inflammatory disease, pelvic congestion syndrome and vulvodynia; vulvovaginal infections, including bacterial vaginosis, candidal vaginitis, trichomonas vaginalis, herpes simplex genital ulcers and warts, pelvic inflammatory disease (PID), cervicitis, acute and chronic salpingitis; endometriosis; gynecological neoplasms, including endometrial Cancer, ovarian cancer, cervical cancer, vulvar cancer, vaginal cancer, fallopian tube cancer and gestational trophoblastic disease; benign tumors; sexually transmitted diseases; sexual dysfunction disorders that respond to pharmacological therapy, including sexual arousal disorder, female orgasmic disorder, dyspareunia and vaginismus; and various gynecological disorders that respond to hormonal therapy.

The foam according to one or more embodiments of the present invention can be used as a lubricating foam. Without limitation, the lubricating foam is useful in lubrication of the birth canal for easy passage of a newborn baby or the vaginal cavity during intercourse.

Rectal applications include, for example, anal abscess/fistula, anal cancer, anal warts, Crohn's disease, haemorrhoids, anal and perianal pruritus, soreness, and excoriation, perianal thrush, anal fissures, fecal incontinence, constipation, polyps of the colon and rectum.

The oleaginous foam compositions of the present invention are further useful for intra-vaginal and rectal treatment of sexually-transmitted and non-sexually-transmitted infectious disease (STDs).

In one or more embodiments, the invention provides a method of treatment of a disorder of the skin, mucosal membrane, ear channel, vaginal, rectal and penile urethra disorders, comprising topical application of the foam composition of the present invention, whereby one or more active agents, in a therapeutically effective concentration to the afflicted area.

In a further embodiment, the invention provides a method of treatment of a non-dermatological disorder, which responds to topical delivery of an active agent, comprising topical application of the foam composition of the present invention, whereby one or more active agents, in a therapeutically effective concentration to the skin.

Treatment/Therapy

The terms "therapy" and "treatment" as used herein interchangeably, cover any treatment of a disease or disorder, and includes, for example:

(i) Curing the disease or disorder;

(ii) preventing the disease or disorder from occurring in a subject which may be predisposed to the disease but has not yet been diagnosed as having it;

(iii) inhibiting the disease or disorder;

(iv) relieving the disease or disorder;

(iv) causing regression of the disease;

(v) providing a beneficial immunological effect;

(vi) improving the quality of life of a subject afflicted by a disease or disorder; and, in the case of cosmetic treatment (vii) cleansing, beautifying, promoting attractiveness, or altering the appearance without affecting the body's structure or functions In the following, some non-limiting examples and experiments are described in detail. This invention is not limited to these examples and experiments. Many variations will suggest themselves are within the full intended scope of the appended claims.

EXAMPLE 1

Anhydrous Foam Comprising a Potent Solvent and MCT Oil

The components of the anhydrous foam are listed in the table below.

| Ingredient | Synonym | Function | % | % | % | % | % |
|---|---|---|---|---|---|---|---|
| n-Methyl pyrrolidone | NMP | Potent solvent | 68.4 | 0 | 0 | 0 | 0 |
| Propylene glycol | | Potent solvent | 0 | 69.5 | 0 | 0 | 0 |
| Glycofurol | | Potent solvent | 0 | 0 | 69.5 | | 69.5 |
| Dimethyl isosorbide | Arlasolve | Potent solvent | 0 | 0 | 0 | 70.0 | 0 |
| MCT oil | Caprylic/Capric Triglycerides | hydrophobic solvent | 9.0 | 9.0 | 9.0 | 9.0 | 9.0 |
| Hexylene glycol | | Co-solvent | 2.1 | 2.1 | 2.1 | 2.1 | 2.1 |
| Glyceryl monostearate | | Stabilizer | 1.8 | 1.8 | 1.8 | 1.8 | 1.8 |
| Stearyl alcohol | | Stabilizer | 1.8 | 1.8 | 1.8 | 1.8 | 1.8 |
| Oleylalcohol | | Foam adjuvant | 2.3 | 2.3 | 2.3 | 2.3 | 2.3 |
| Sisterna SP-30 | Sucrose ester | Surfactant | 0.9 | 0.9 | 0.9 | 0.9 | 0.9 |
| Sisterna SP70 | Sucrose ester | Surfactant | 0.9 | 0.9 | 0.9 | 0.9 | 0.9 |
| Klucel MF | Hydroxypropyl methylcellulose | Gelling agent | 0.4 | 0.4 | 0.4 | 0.4 | 0.4 |
| Phenonip | Methyl, butyl, propyl paraben, phenoxyethanol | Preservative | 0.3 | 0.3 | 0.3 | 0.3 | 0.3 |
| Betamethasone valerate | | Active agent | 0.1 | 0 | 0 | 0 | 0 |
| Mupirocin | | Active agent | 0 | 1.0 | 0 | 0 | 0 |
| Ketoconazole | | Active agent | 0 | 0 | 1.0 | 0 | 0 |
| Cyclosporine | | Active agent | 0 | 0 | 0 | 0.5 | 0 |
| Acyclovir | | Active agent | 0 | 0 | 0 | 0 | 5 |
| Propane/butane | | Propellant | 12.0 | 10.0 | 10.0 | 10.0 | 10.0 |

Note:

The liquefied or gas propellant can be added at a concentration of about 3% to about 25%.

The compositions used only non-ionic surface active agents, in a concentration of about 2%, and the total amount of surface active agent, foam adjuvants and polymeric agent ranged from about 4% to about 6% (w/w).

The foam of this example having a density of about 0.2 gr/mL is useful as a carrier of additional active agents. It is also useful as lubricating foam, for various purposes.

EXAMPLE 2

MCT Oil Foams

The components of the oil/glycerin foam are listed in the table below.

| Ingredient | Synonym | Function | % | % | % | % | % | % |
|---|---|---|---|---|---|---|---|---|
| Caprylic/Capric Triglycerides | MCT oil | hydrophobic solvent/potent solvent | 60.9 | 60.0 | 59.0 | 60.0 | 60.0 | 56.0 |
| Propylene glycol | | Co-solvent/poten solvent | 10.0 | 10.0 | | | 5.0 | 5.0 |
| Hexylene glycol | | Co-solvent/poten solvent | | | 10.0 | 5.0 | | |
| Purified water | De-ionized Distilled water | Solvent | 10.0 | 10.0 | 10.0 | 10.0 | 10.0 | 10.0 |
| Potent solvent | | | — | — | — | 5.0 | 5.0 | 5.0 |
| Lecithin | Phospholipids | Surfactant | 10.0 | 10.0 | 10.0 | 10.0 | 10.0 | 10.0 |
| Stearyl alcohol | Stearyl alcohol | Stabilizer | 5.0 | 5.0 | 5.0 | 5.0 | 5.0 | 5.0 |
| Glyceryl monostearate | Glyceryl monostearate | Stabilizer | 2.0 | 2.0 | 2.0 | 2.0 | 2.0 | 2.0 |
| PVP K90 | Polyvinyl pyrrolidone | Gelling agent | 2.0 | 2.0 | 2.0 | 2.0 | 2.0 | 2.0 |
| Preservative | | | 0.3 | 0.3 | 0.3 | 0.3 | 0.3 | 0.3 |

-continued

| Ingredient | Synonym | Function | % | % | % | % | % | % |
|---|---|---|---|---|---|---|---|---|
| Betamethasone valerate | | Active agent | 0.1 | | | | | |
| Mupirocin | | Active agent | | 1.0 | | | 1.0 | |
| Ketoconazole | | Active agent | | | 2.0 | | | |
| Tacrolimus | | Active agent | | | | 1.0 | | |
| Acyclovir | | Active agent | | | | | | 5.0 |
| Propane/butane | | Propellant | 12.0 | 10.0 | 10.0 | 10.0 | 10.0 | 10.0 |

Notes:
- The liquefied or gas propellant can be added at a concentration of about 3% to about 25%.
- The potent solvent and hexylene glycol (emollient) may be optionally incorporated.
- In these particular examples, the water content was minimal and necessary for the gelling agent incorporation; higher levels of water are an option.
- Lecithin is provided as the surfactant. Several types of powdered, de-oiled and liquid (55% to 80% Phosphatidyl choline) phospholids have been tested successfully for the production of acceptable foams.
- In certain examples, polyvinylpyrrolidone (PVP) was shown to be the preferred gelling agent.
- The compositions use only non-ionic surface active agents, in concentration of about 2%, and the total amount of surface active agent, foam adjuvants and polymeric agent ranged from about 4% to about 6% (w/w).
- The foam of this example is useful as a carrier of additional active agents. It is also useful as lubricating foam, for various purposes.
- Stearyl alcohol, cetyl alcohol or oleyl alcohol (foam adjuvants) and co-solvents, such as propylene glycol and hexylene glycol, are optionally incorporated in the foam.
- Density of the foam is about 0.08 to about 0.12 gr/mL

EXAMPLE 3

Oil/glycerin Foam

The components of the oil/glycerin foam are listed in the table below.

| Ingredient | Synonym | Function | % | % | % | % |
|---|---|---|---|---|---|---|
| Glycerin | Glycerol | Co-solvent | 32.0 | 32.0 | 32.5 | 40.5 |
| Purified water | | Solvent | 17.0 | 17.0 | 18.55 | 14.05 |
| MCT oil | Caprylic/Capric Triglycerides | Hydrophobic Solvent | 9.0 | 9.0 | 9.0 | 8.0 |
| Isopropyl myristate | IPM | Co-solvent | 0 | 0 | 9.0 | 8.0 |
| Isopropyl palmitate | IPP | Co-solvent | 0 | 10.0 | 0 | 0 |
| Diisopropyl adipate | DISPA | Co-solvent | 9.0 | 0 | 0 | 0 |
| Hexylene glycol | Hexylene glycol | Emollient | 9.0 | 9.0 | 9.0 | 8.0 |
| Oleyl alcohol | Oleyl alcohol | Foam adjuvant | 9.0 | 9.0 | 9.0 | 8.0 |
| Sisterna sp-50 | Sucrose ester | Surfactant | 1.8 | 1.8 | 1.8 | 1.8 |
| Glyceryl monostearate | Glyceryl monostearate | Stabilizer | 0.4 | 0.4 | 0.4 | 0.4 |

-continued

| Ingredient | Synonym | Function | % | % | % | % |
|---|---|---|---|---|---|---|
| Pemulen TR2 | Acrylates/C10–30 Alkyl Acrylate Cross-Polymer | Stabilizer | 0.1 | 0.1 | 0.1 | 0.1 |
| Methocel K100M | Methyl cellulose | Gelling agent | 0.3 | 0.3 | 0.3 | 0.3 |
| TEA | Triethanolamine | Neutralizer | 0.05 | 0.05 | 0.05 | 0.05 |
| Phenonip | Methyl, butyl, propyl paraben, phenoxyethanol | Preservative | 0.25 | 0.35 | 0.3 | 0.3 |
| Betamethasone valerate | | Active agent | 0.1 | 0 | 0 | 0 |
| Mupirocin | | Active agent | 0 | 1.0 | 0 | 0 |
| Ketoconazole | | Active agent | 0 | 0 | 2.0 | 0 |
| Cyclosporine | | Active agent | 0 | 0 | 0 | 0.5 |
| Propane/butane | | Propellant | 12.0 | 10.0 | 8.0 | 10.0 |

Notes:
- The liquefied or gas propellant can be added at a concentration of about 3% to about 25%.
- In non-limiting examples, the oivglycerin foams of the present invention comprise about 10% to about 20% water, about 37% glycerin and about 30% oil blend and about 10% hexylene glycol.
- The compositions use only non-ionic surface active agents, in concentration of about 2%, and the total amount of surface active agent, foam adjuvants and polymeric agent ranged from about 8% to about 12% (w/w).
- The foam of this example is useful as a carrier of additional active agents. It is also useful as lubricating foam, for various purposes.
- Density of the foam is about 0.18 gr/mL to about 0.20 gr/mL.
- Upon release from the aerosol can, foam is released, and stays stable for several minutes, until it is rubbed onto the afflicted area, then it is immediately broken down and absorbed. This property enables convenient and even application with good sensory feeling.

EXAMPLE 4

Compositions Comprising PEG

Compositions comprising polyethylene glycol (PEG) derivatives have been prepared and shown to be excellent foams. According to the following non-limiting example the composition comprises about 80% to about 97.5% PEG 400, about 1% to about 5% of at least one surface active agent having HLB between 2 and 9 and 0.5% gelling agent, prior to the addition of a propellant (about 10% of the total composition). Notably the following compositions did not comprise any water at all.

| PEG 400 foamable compositions (Vehicle) | | | | | | | |
|---|---|---|---|---|---|---|---|
| | % w/w | % w/w | % w/w | % w/w | % w/w | % w/w | % w/w |
| PEG400 | 87.50 | 91.50 | 87.50 | 89.50 | 87.50 | 87.50 | 87.50 |
| Klucel MX (hydroxypropyl cellulose) | 0.50 | 0 | 0.50 | 0 | 0.50 | 0 | 0.50 |
| Klucel LF (hydroxypropyl cellulose) | 0 | 0.50 | 0 | 0.50 | 0 | 0.50 | 0 |
| Lipocol C2 (POE (2) cetyl ether) | 2.00 | 2.00 | 0 | 0 | 0 | 0 | 0 |
| Myrj 52 | 0 | 0 | 2.00 | 2.00 | 0 | 0 | 0 |
| Steareth-2 | 0 | 0 | 0 | 0 | 2.00 | 2.00 | 0 |
| Dermofeel G10 (Polyglyceryl-10 Laurate) | 0 | 0 | 0 | 0 | 0 | 0 | 2.00 |
| Propellant | 10 | 6 | 10 | 8 | 10 | 10 | 10 |
| Density | 0.060 | 0.063 | 0.063 | 0.055 | 0.052 | 0.050 | 0.075 |

Notes:
The liquefied or gas propellant can be added at a concentration of about 3% to about 25%.
The foams of this example have a non-ionic surface active agent at a concentration of 2%. Total amounts of surface active agent foam adjuvant and polymeric agent is in the range of 2.5%.
The compositions are useful as carriers of various active therapeutic active agents.
The following table exemplifies the use of PEG 400 as a potent solvent for Mupirocin, which is practically insoluble in mineral oil and other commonly used ointment solvents. Note that Mupirocin is incompatible with most solvents and thus, a foam comprising PEG 400 as the sole solvent is highly valuable.

| PEG 400 foamable compositions, comprising Mupirocin | | |
|---|---|---|
| | % w/w | % w/w |
| Mupirocin | 2.00 | 2.00 |
| PEG400 | 89.50 | 89.50 |
| Klucel LF (hydroxypropyl cellulose) | 0.50 | 0.50 |
| Steareth-2 | 2.00 | 0 |
| Polyglyceryl-10 Laurate | | 2.00 |
| Propellant (Propane/butane)* | 6.0 | 6.0 |
| Density | 0.060 | 0.062 |

Notes:
*The liquefied or gas propellant can be added at a concentration of about 3% to about 25%.
**The foams of this example have a non-ionic surface active agent at a concentration of 2%. Total amounts of surface active agent foam adjuvant and polymeric agent is in the range of 2.5% (w/w).

What is claimed is:

1. An oleaginous foamable therapeutic composition, comprising:
 a. about 70% to about 96.5% of a solvent phase, wherein the solvent phase comprises:
  i) a hydrophobic solvent, a silicone oil, or a mixture thereof and
  ii) optionally an emollient, a co-solvent, or a mixture thereof
 b. at least a non-ionic surface-active agent at a concentration of about 0.1% to less than about 10% by weight of the total composition;
 c. at least one gelling agent at a concentration of about 0.1% to about 5% by weight of the total composition;
 d. a therapeutically effective amount of at least one active agent; and
 f. at least one liquefied or compressed gas propellant, at a concentration of about 3% to about 25% by weight of the total composition,
 wherein the composition forms a breakable foam upon dispensing that collapses upon application of shear force; and
 wherein the specific gravity of the foam is less than about 0.5 g/mL; and
 wherein the water content of the composition is less than about 30% by weight.

2. The oleaginous composition of claim 1, comprising less than about 5% of a lower alcohol, having up to 5 carbon atoms in its carbon chain skeleton.

3. The oleaginous composition of claim 1, further comprising a foam adjuvant selected from the group consisting of fatty alcohols having greater than or equal to 15 carbons and fatty acids having greater than or equal to 16 carbons.

4. The oleaginous composition of claim 1, wherein the hydrophobic solvent has solubility in distilled water at ambient temperatures of less than about one gram per 100 mL.

5. The oleaginous composition of claim 1, wherein the hydrophobic solvent is selected from the group consisting of mineral oil, triglyceride oil, an ester of a fatty acid, an ester of a decarboxylase acid, polyunsaturated oil, unsaturated oil, and an essential oil.

6. The oleaginous composition of claim 1, wherein the solvent phase comprises a mixture of at least one hydrophobic solvent and at least one co-solvent.

7. The oleaginous composition of claim 6, wherein the mixture of at least one hydrophobic solvent and the at least one co-solvent comprises a weight ratio of about 1:8 to about 8:1.

8. The oleaginous composition of claim 7, wherein the mixture forms an emulsion.

9. The oleaginous composition of claim 7, wherein the at least one co-solvent comprises glycerin.

10. The oleaginous composition of claim 9, wherein the mixture of at least one hydrophobic solvent and glycerin comprises a weight ratio of about 1:4 to about 4:1.

11. The oleaginous composition of claim 9, wherein the mixture of at least one hydrophobic solvent and glycerin comprises a weight ratio of about 1:2 to about 2:1.

12. The oleaginous composition of claim 1 or 6, wherein the co solvent is polyethyelene glycol.

13. The oleaginous composition of claim 1, further comprising an ionic surface-active agent, wherein the mixture of the non-ionic surface-active agent and the ionic surface-active agent is present at a weight ratio of about 20:1 to about 1:1 non-ionic surface-active agent to ionic surface-active agent.

14. The oleaginous foam able composition of claim 1, wherein the concentration of the nonionic surfactant is from about 0.1% to less than about 2%.

15. The oleaginous composition of claim 1, wherein the at least one gelling agent is one or more gelling agents selected from the group consisting of natural polymeric materials, semi-synthetic polymeric materials, synthetic polymeric materials, inorganic gelling agents and mixtures thereof.

16. The oleaginous composition of claim 1, wherein the water content is less than about 20% by weight.

17. The oleaginous composition of claim 1, wherein the composition is contained within a pressurized container.

18. The oleaginous composition of claim 1 wherein the specific gravity of the foam is about 0.01 gr/ml to about 0.3 gr/mL upon release from the pressurized container.

19. The oleaginous composition of claim 1, wherein the active agent is selected to treat a dermatological or mucosal disorder that is bacterial, fungal, viral, parasitic, inflammatory, autoimmune, allergic, hormonal, malignant and combinations thereof.

20. The oleaginous composition of claim 1 wherein the active agent is a component of the foamable composition selected from a solvent, a surface-active agent, a gelling agent and a foam adjuvant.

21. The oleaginous composition of claim 1, wherein the at least one active agent is selected from a therapeutic agent and a cosmetic agent.

22. The oleaginous composition of claim 21, wherein the at least one therapeutic agent is selected from an anti-infective, an antibiotic, an antibacterial agent, an antifungal agent, an antiviral agent, an antiparasitic agent, an antiinflammatory agent, an immunosuppressive agent, and immunomodulator, an immuno regulating agent, an anesthetic, an analgesic, an antiallergic agent, a corticosteroid, a retinoid, an antiproliferative agent, an anticancer agent, a photodynamic therapy agent, a lubricating agent and mixtures thereof.

23. The oleaginous composition of claim 22, wherein the therapeutic agent is selected for the treatment of a disorder of the skin, mucosal membrane, ear channel, vagina, penile urethra, colon and rectum.

24. The oleaginous composition of claim 22, wherein the cosmetic agent is selected from a retinoid, an anti-wrinkle agent, a radical scavenger, a self-tanning agent, a skin whitening agent, a skin protective agent, an anti-cellulite agent, a massaging oil and an anti-wart agent.

25. The oleaginous composition of claim 22, wherein the therapeutic agent is intended for transdermal delivery.

26. The oleaginous composition of claim 1, wherein the at least one active agent is an inorganic solid matter.

27. The oleaginous composition of claim 26, wherein the inorganic solid matter is a metal oxide for forming a protective layer on a body surface or a mucosal membrane.

28. The oleaginous foamable composition of claim 1, wherein the composition is a water-in-oil emulsion.

29. The oleaginous composition of claim 28, wherein the at least one nonionic surfactant is a non-ionic lipophilic surfactant having an HLB value of about 3 to about 10.

30. The oleaginous composition of claim 29, comprising less than about 5% of a lower alcohol, having up to 5 carbon atoms in its carbon chain.

31. The oleaginous emulsion of claim 29, further comprising a foam adjuvant selected from the group consisting of fatty alcohols having greater than or equal to 15 carbons and fatty acids having greater than or equal to 16 carbons.

32. The oleaginous composition of claim 29, wherein the hydrophobic solvent has solubility in distilled water at ambient temperatures of less than about one gram per 100 mL.

33. The oleaginous composition of claim 32, wherein the hydrophobic solvent is selected from the group consisting of mineral oil, triglyceride oil, an ester of a fatty acid, an ester of a dicarboxylic acid, polyunsatured oil, unsaturated oil, and an essential oil.

34. The oleaginous emulsion of claim 29, wherein the at least one hydrophobic solvent and water are present at a weight ratio in the range of about 1:3 to about 6:1.

35. The oleaginous foam able composition of claim 29, wherein the concentration of the nonionic lipophilic surfactant is from about 0.1% to less than about 2%.

36. The oleaginous foam able composition of claim 35, wherein the non-ionic lipophilic surfactant is selected from the group consisting of soribitan derivatives, alkoxylated alcohols, hydroxylated derivatives of polymeric silicones, alkylated derivatives of hydroxylated polymeric silicones, glyceryl esters, beeswax derivatives, lecithin and mixtures thereof.

37. The oleaginous emulsion of claim 29, wherein the at least one gelling agent is selected from the group consisting of natural polymeric materials, semi-synthetic polymeric materials, synthetic polymeric materials, inorganic gelling agents and mixtures thereof.

38. The oleaginous emulsion of claim 37, wherein the inorganic gelling agent comprises silicone dioxide.

39. The oleaginous emulsion of claim 29, having a specific gravity of about 0.01 gr/ml to about 0.3 gr/mL, upon extrusion from a pressured container.

40. The oleaginous emulsion of claim 29, wherein the at least one active agent is a component of the foamable composition and is selected from a solvent, a surface-active agent, a gelling agent and a foam adjuvant.

41. The oleaginous emulsion of claim 29 wherein the at least one active agent is selected from an anti-infective, an antibiotic, an antibacterial agent, an antifungal agent, an antiviral agent, an antiparasitic agent, an antiinflammatory agent, an anesthetic, an analgesic, an antiallergic agent, a corticosteroid, a retinoid, an antiproliferative agent, an anticancer agent, a photodynamic therapy agent, an anti-wrinkle agent, a radical scavenger, a self-tanning agent, a skin whitening agent, a skin protective agent, an anti-cellulite agent, a massaging oil and an anti-wart agent, a refatting agent, a lubricating agent and mixtures thereof.

42. The oleaginous composition of claim 29, wherein the active agent is selected for the treatment of a disorder of the skin, mucosal membrane, ear channel, vagina, penile urethra, and rectum.

43. The oleaginous emulsion of claim 29, wherein the active agent is intended for transdermal delivery.

44. The oleaginous emulsion of claim 29, having the properties of breakable foam for treating, alleviating or preventing a dermatological or mucosal disorder.

45. The oleaginous composition of claim 44, wherein the etiology of the dermatological or mucosal disorder is bacterial, fungal, viral, parasitic, inflammatory, autoimmune, allergic, hormonal, malignant, and combinations thereof.

46. The oleaginous emulsion of claim 29, wherein the at least one active agent is an inorganic solid matter.

47. The oleaginous emulsion of claim 46, wherein the inorganic solid matter is selected to form a protective layer on a body surface or a mucosal membrane.

48. The oleaginous emulsion of claim 46, wherein the inorganic solid matter is selected to treat a skin disorder selected from sensitive skin, diaper rash and diaper dermatitis.

49. The oleaginous emulsion of claim 46, further comprising at least one active agent, selected from antibacterial agent, antifungals agent and anti-inflammatory agent.

50. A method of treating, alleviating or preventing a dermatological, cosmetic or mucosal disorder, comprising administering topically to a subject having said disorder a therapeutically effective amount of an oleaginous foam composition according to claim 1.

51. The oleaginous foam able composition of claim 1, further comprising a phospholipids non-ionic surfactant at concentration of about 0.1% to about 25% by weight of the total composition.

52. The oleaginous composition of claim 51 wherein the phospholipid comprises phosphatidylchlorine.

53. The composition of claim 51, wherein the phospholipid comprises lecithin.

54. A therapeutic device, comprising a pressurized can, equipped with a metered dose valve and an actuator capable of dispensing a foam, and containing an oleaginous foam composition according to claim 1 or claim 29.

55. The device of claim 54, wherein the metered dose valve provides a unit dose of between about 10 μL and about 1000 μL.

56. The device of claim 54, wherein the metered dose valve provides a unit dose of between about 50 μL and about 250 μL.

57. The oleaginous foamable therapeutic composition of claim 1, wherein said co-solvent is one or more co-solvents selected from the group consisting of polyols, sulfoxides, oleates, lactam compounds, esters, amides, alkanoic acids, and alkanols and admixtures thereof.

58. The oleaginous foamable therapeutic composition of claim 1, further comprising an ionic surface-active agent.

59. The oleaginous foamable therapeutic composition of claim 1, wherein said active agent is selected to treat a dermatological or mucosal disorder.

60. The oleaginous foamable therapeutic composition of claim 26, wherein the inorganic solid matter comprises a metal oxide.

61. The oleaginous foamable water-in-oil emulsion of claim 29, wherein said co-solvent is one or more co-solvents selected from the group consisting of polyols, sulfoxides, oleates, lactam compounds, esters, amides, alkanoic acids, and alkanols and admixtures thereof.

62. The oleaginous foamable water-in-oil emulsion of claim 61, wherein the gelling agent is one or more gelling agents selected from the group consisting of natural polymeric materials, semi-synthetic polymeric materials, synthetic polymeric materials, inorganic gelling agents and mixtures thereof.

63. The oleaginous foamable water-in-oil emulsion of claim 62, wherein the inorganic gelling agent comprises silicone dioxide.

64. The oleaginous foamable water-in-oil emulsion of claim 29, having a specific gravity of about 0.02 gr/ml to about 0.4 gr/mL, upon extrusion from a pressured container.

65. The oleaginous foamable water-in-oil emulsion of claim 29 comprising less than about 5% of a short chain alcohols having up to 5 carbon atoms in the short chain alcohol carbon chain.

66. The oleaginous foamable therapeutic composition of claim 51, further comprising an ionic surface-active agent.

67. The oleaginous composition of claim 1, wherein the co-solvent solubilizes the active agent substantially better than mineral oil solubilizes the active agent.

* * * * *